US008822737B2

(12) United States Patent
Houseman et al.

(10) Patent No.: US 8,822,737 B2
(45) Date of Patent: Sep. 2, 2014

(54) GLYCEROL DERIVED MATERIAL

(75) Inventors: Richard Alwyn Houseman, Yorkshire (GB); Abraham Christo Venter, Reading (GB)

(73) Assignee: Bio-Energy Ingredients Limited (GB)

( * ) Notice: Subject to any disclaimer, the term of this patent is extended or adjusted under 35 U.S.C. 154(b) by 565 days.

(21) Appl. No.: 13/002,760

(22) PCT Filed: Jul. 6, 2009

(86) PCT No.: PCT/IB2009/052931
§ 371 (c)(1),
(2), (4) Date: May 16, 2011

(87) PCT Pub. No.: WO2010/004501
PCT Pub. Date: Jan. 14, 2010

(65) Prior Publication Data
US 2011/0256290 A1  Oct. 20, 2011

(30) Foreign Application Priority Data

Jul. 7, 2008 (ZA) ................................. 2008/05911

(51) Int. Cl.
*C07C 29/70* (2006.01)
*A23K 1/16* (2006.01)
*A23K 1/175* (2006.01)
*C11C 3/00* (2006.01)
*C11C 1/02* (2006.01)

(52) U.S. Cl.
CPC ............. *C07C 29/70* (2013.01); *A23K 1/1646* (2013.01); *A23K 1/1609* (2013.01); *A23K 1/1753* (2013.01); *C11C 3/003* (2013.01); *A23K 1/1634* (2013.01); *C11C 1/025* (2013.01)
USPC ............ 568/698; 568/697; 568/699; 568/700

(58) Field of Classification Search
CPC ......... C08K 5/057; C07C 29/70; C07C 31/30
USPC ............. 426/99, 553; 568/697, 698, 699, 700
See application file for complete search history.

(56) References Cited

U.S. PATENT DOCUMENTS

| 5,709,849 | A  | * | 1/1998 | Ito et al. ........................... 424/63 |
| 6,229,031 | B1 | * | 5/2001 | Strohmaier et al. ........... 554/156 |
| 2005/0171367 | A1 | * | 8/2005 | DeLoach ......................... 554/78 |
| 2005/0233009 | A1 | * | 10/2005 | Kemp et al. .................... 424/696 |

FOREIGN PATENT DOCUMENTS

EP           1447383 A1   8/2004
WO   WO2007/077266 A1   7/2007

OTHER PUBLICATIONS

Ayhan Demirbas, "Biodiesel from Sunflower Oil in Supercritical Methanol with Calcium Oxide"—Energy Conversion and Management, vol. 45, pp. 937-941 (Oct. 2, 2006).
Masato Kouzu, "Calcium Oxide as a Solid Base Catralyst for Transesterfication of Soybean Oik and its Application to Biodiesel Production"—Fuel, vol. 87 (Nov. 20, 2007).
Fujii et al., Calcium Glyceroxides formed in the system of calcium oxide-glycerol; Zeitschrift fur anorganische und allgemeine Chemie; 2004, vol. 359, Issue 5-6, pp. 296-304.
Kouzu et al., "Active phase of calcium oxide used as solid base catalyst for transesterification of soybean oil with refluxing methanol," Applied Catalysis A: General, vol. 334 (2008) pp. 357-365.
PCT/IB2009/052931 Search Report and Written Opinion mailed Apr. 14, 2010.
PCT/IB2009/052931 IPRP dated Oct. 14, 2010.

* cited by examiner

*Primary Examiner* — Sudhakar Katakam
*Assistant Examiner* — Pancham Bakshi
(74) *Attorney, Agent, or Firm* — Wilson Sonsini Goodrich & Rosati

(57) ABSTRACT

A method of producing a solid glycerol derived material includes the steps of combining glycerol with a metal oxide, the glycerol having a water content of between about 5 and 50%, and the rate of combination of the glycerol and the metal oxide and the amount of the metal oxide being selected so that at least part of the water present in the glycerol reacts with the metal oxide in an exothermic reaction and at least part is driven off by heat produced in the exothermic reaction to produce the solid glycerol derived material.

19 Claims, No Drawings

GLYCEROL DERIVED MATERIAL

CROSS-REFERENCE TO RELATED APPLICATIONS

This application claims the benefit of International Patent Application PCT/IB2009/052931 filed 6 Jul. 2009, which claims priority to South African Patent Application No. 2008/05911, entitled A GLYCEROL DERIVED MATERIAL, filed 7 Jul. 2008, the contents of the application are incorporated herein by reference in their entirety.

THIS INVENTION relates to an energy efficient method of producing solid glycerol derived materials from wet glycerol and to solid glycerol derived materials produced by the method.

One of the objects of the present invention is to convert a liquid mixture of glycerol and water into a non-liquid product. For the purposes of this specification, "solid glycerol derived materials" should be understood to include materials in the form of powders, granules, flakes, particles, pieces and the like as well as materials which are semi-solid materials i.e. materials which do not flow easily or at all, such as gums, pastes, creams, gummy granules and the like.

Bio-diesel can be produced from vegetable oils or animal fats by trans-esterification using an alcohol and a base, and glycerol is produced as a by-product of the production. Commonly, the vegetable oil or animal fat is reacted with an alcohol such as methanol in the presence of a base such as sodium hydroxide or potassium hydroxide, or the corresponding methoxide. Bio-diesel can be produced in a single stage or a two stage reaction process but, in either process, one of the by-products is glycerol which constitutes between about 10-20% of the total mass of the product. The glycerol is usually separated from the bio-diesel by settling prior to washing the bio-diesel with water. The glycerol which is produced from this process is impure and contains unreacted methanol, sodium or potassium salts, water and other impurities caught up in the settling process. This glycerol is, accordingly, an undesirable by-product of the production of bio-diesel, but very large quantities of glycerol are nevertheless produced in the bio-diesel industry. In addition, glycerol derived from other sources often contains water and other impurities.

Prior art processes for the purification of glycerol produced, for example, in the manufacture of bio-diesel have involved heating the glycerol, optionally under vacuum, to recover unreacted methanol. However it has been found that it is difficult to remove all of the methanol because the mixture gradually thickens with increasing methanol loss and the glycerol remaining after most of the methanol has been removed can be as thick as syrup. However, the glycerol can be as thin as a light engine oil, depending upon the temperature, moisture content and methanol content. It is an object of the invention to address the problem of drying, recovering, purifying and using glycerol produced in processes such as the production of bio-diesel or the commercial manufacture of glycerol.

According to a first aspect of the invention, there is provided a method of producing a solid glycerol derived material, the method including the step of combining glycerol with a metal oxide, the glycerol having a water content of between about 5% and 50%, and the rate of combination of the glycerol and the metal oxide and the amount of the metal oxide being selected so that at least part of the water present in the glycerol reacts with the metal oxide in an exothermic reaction and at least part is driven off by heat produced in the exothermic reaction to produce the solid glycerol derived material.

The glycerol may be glycerol produced in the manufacture of bio-diesel. It may, instead, be glycerol derived from other processes.

Typically, the glycerol will have a water content of between about 9% and 18% (w/w).

The metal oxide may be selected from calcium oxide, magnesium oxide, burnt caustic magnesia, other Group 1A or 2A or transition metal oxides or blends thereof. Preferably, the metal oxide will be calcium oxide or quick lime. The metal oxide may instead include one or more metal hydroxides.

In an embodiment of the invention the metal oxide may be combined with a metal hydroxide in order to control the exotherm produced when the metal oxide reacts with the water. For example, if the metal oxide is calcium oxide, the calcium oxide may be combined with a predetermined amount of calcium hydroxide or other metal hydroxide in order to control the exotherm. The terms calcium oxide or metal oxides in the context of this specification accordingly include within their scope oxides containing hydroxides.

If the glycerol is derived from bio-diesel production, it may include an alcohol such as methanol and other by-products produced in the trans-esterification process.

The method may include the prior step of determining the quantities of water and alcohol in the glycerol. Various factors will affect the amount of metal oxide required. These may include, amongst others, the purity of the metal oxide, the reactivity of the metal oxide, the amount of other oxides present in the metal oxide and the amount of water present in the glycerol. The reactivity of the metal oxide will be determined by the purity and the state of division of the metal oxide, the purer and the more finely-divided the material, the more reactive it will be. The calcium oxide used in the method of the invention will typically have a purity above about 75%. Preferably the purity will be between about 85% and 100% and more preferably between about 90% and 100%.

The amount of water present will, in turn, determine the amount which will react with the calcium oxide to produce calcium hydroxide and the amount that will be evaporated as a result of the exothermic reaction between the calcium oxide and the water.

The amount of water per 1 molar equivalent of the metal oxide, the metal hydroxide of a mixture of the metal oxide and metal hydroxide in the process of the invention with or without the inclusion of an additional component or additional components may be between about 0.1 and 10 and will preferably be between about 0.4 and 6. More preferably it will be between 0.5 and 3 molar equivalents.

The solid product produced in the invention may be a particulate or powdery material.

The invention thus provides a method of using glycerol, for example glycerol which is produced as a by-product in the production of bio-diesel, but also glycerol produced by other processes, to produce in an energy efficient manner a solid glycerol derived material and, preferably, a dry particulate material which can be used as a source of glycerol or as an intermediate for other purposes.

It is a particular object of the invention to provide, from wet glycerol produced in the manufacture of bio-diesel, a material which can be used as an animal feedstuff or which can be combined with other feedstuff components as a feedstuff supplement to produce an animal feedstuff. The method of the invention may thus be conducted in the presence of one or more additional components which will provide, for example, a phosphate, sulphate or chloride in the glycerol derived material, or an organic component such as an organic salt or acid. The glycerol derived material will then be suitable for use as an animal feedstuff or in an animal feedstuff.

The method may thus include combining the glycerol and the metal oxide with at least one additional component, the or each additional component being selected from inorganic and organic acids. The inorganic acids may be selected from phosphoric acid, sulphuric acid and hydrochloric acid. The organic acids may be selected from alkyl carboxylic acids, hydroxyalkyl carboxylic acids, amino acids and derivatives, precursors or analogues thereof. For example the organic acids may be selected from propionic acid, lactic acid, palmitic acid and stearic acid. The invention is, however, not limited to inorganic or organic acids and any material which is compatible with the reaction conditions of the invention and which would be, or would produce, a suitable animal feedstuff additive may be used.

The additional component or components may be a material which will react exothermically with a metal oxide and/or a metal hydroxide in an aqueous glycerol medium to provide the heat to transform the liquid into a solid product, with the glycerol either present as a spectator supported on the solid product or forming part of the new solid product or chemical entity.

Thus, when no additional component is used, the reaction of the metal oxide or mixture of metal oxide and metal hydroxide with water and glycerol produces a solid product. The exotherm is generated by the reaction of the metal oxide with water and to a lesser extend the reaction of the hydroxide which is formed with glycerol. The glycerol is then transformed into a metal glyceroxide or a mixture of metal glyceroxides which are solid materials.

If an inorganic acid such as phosphoric acid is used in the method of the invention using either a metal oxide or a mixture of metal oxide(s) and metal hydroxide(s) with water and glycerol, the exotherm is generated through the reaction of the metal oxide with water but additionally also through the reaction of the inorganic acid with the oxide and/or hydroxide which results in a higher and faster exotherm than that obtained without the addition of phosphoric acid. In this case, the main reaction (depending on reagent ratios) is the formation of an inorganic metal salt such as calcium phosphate. In this case, the glycerol is mainly present as an unreacted spectator supported on the inorganic salt matrix. The glycerol may to some extent (depending on the reagent ratios and reaction conditions) react with the acid but no calcium glycerol phosphate has been detected in the solid products produced when phosphoric acid is used as the additional component.

If an organic acid, such as palmitic acid, is used as the additional component, the main reaction is the formation of an organic metal salt such as calcium palmitate which forms the solid component in the product and the glycerol is supported on this solid component. The glycerol may again be present as an unreacted spectator supported on the solid organic salt or it may react with the organic acid depending on reagent ratios form a mono-, and/or di- and/or tri-ester.

The molar ratio between the additional component (for example the phosphoric acid, sulphuric acid or propionic acid) per 1 molar equivalent of metal oxide or metal oxide-metal hydroxide mixture may be between about 0.001 and 2 molar equivalents and is preferably between about 0.1 and 1 molar equivalent.

The addition of any suitable additional component which reacts with the water and/or glycerol in an exothermic manner to give a solid product in which the glycerol is present as a spectator and/or part of a new chemical entity which is supported on the solid product, is accordingly included within the scope of the invention.

Accordingly, the invention allows for the manipulation or adjustment of the chemistry by the addition of an additive or mixture of additives to provide products of which the respective components meet specific requirements for its intended use, such as regulatory approval of individual components and/or nutritional value in animal nutrition applications or desired chemical and/or physical properties for intended applications.

The additive or additives may be added in various amounts at any stage of the reaction depending on the desired outcome and as indicated above may be a substance or substances which would be highly reactive towards the metal oxide or metal hydroxide which forms in the reaction of the starting metal oxide with water in the water-glycerol mixture and may or may not be reactive towards starting glycerol.

According to a second aspect of the invention there is provided a method of producing an animal feedstuff or animal feedstuff supplement, the method including the steps of combining glycerol with a metal oxide and optionally a metal hydroxide and at least one additional component, the glycerol having a water content of between 5% and 50%, and the rate of combination of the glycerol and the metal oxide and the amount of the metal oxide being selected so that at least part of the water present in the glycerol reacts with the metal oxide in an exothermic reaction and at least part is driven off by heat produced in the exothermic reaction to produce the animal feedstuff or feedstuff supplement, the or each additional component being selected from inorganic acids, organic acids and mixtures thereof.

The inorganic and organic acids may be as hereinbefore described.

The product may be an animal feedstuff in its own right or, preferably, will be combined with other animal feedstuff components to act as a fortifying component or nutritional additive in the animal feedstuff. The invention thus provides a method of converting what would otherwise be a waste material into a valuable animal feedstuff or animal feed supplement by simply reacting the waste material i.e. the water/glycerol mixture, with a base such as calcium oxide and an acid such as phosphoric acid to produce the feedstuff or supplement.

The utilisation of inorganic acids as additives is described, in Examples 9 to 20 and the utilisation of organic acids as additives is described in Examples 21 to 24.

Based on stoichiometric calculations, approximately 56 g of pure calcium oxide will react with 18 g of water to produce 74 g of calcium hydroxide. Accordingly, 1 g of calcium oxide will "bind" with 0.321 g of water. Alternatively, 1 g of water will require 3.11 g of calcium oxide. However, this does not take into account the affect of the exothermic reaction between calcium oxide and water, and some water, over and above that consumed in forming calcium hydroxide, will be driven off by the heat of the exothermic reaction.

The amount of water driven off during the exothermic reaction will be affected by the factors outlined above, namely purity and reactivity of the calcium oxide, the level of metal oxide such as magnesium oxide trapped in the calcium oxide, impurities in the water, the altitude above sea level, heat losses from the system and the like.

In practice it has been found that the amount of calcium oxide required to drive off 1 g of water ranges between about 1.0 g-3.5 g.

There are different ways in which the method of the invention can be carried out. In one embodiment, the wet glycerol and the calcium oxide and, optionally, the additional component are rapidly combined over a period of between about 1 and 10 seconds, the reaction mixture is rapidly agitated for a period of between about 1 and 30 seconds and the reaction mixture is then rapidly discharged over a period of between about 1 and 20 seconds into a suitable vessel or container. In this process, the mixture is allowed to stand so that the reaction can continue until a particulate or powdery product is produced. This can take between about 5 and about 60 minutes. Because of the rapid reaction and the rapid temperature rise, this process can lead to some loss of the glycerol. The time intervals set out in respect of this embodiment of the invention are typical for small-scale reactions and were found to vary depending upon the scale of the operation, the amount of water present in the mixture, the reactivity of the metal oxide, the presence of an additional component and the like.

In another embodiment, a predetermined quantity of wet glycerol and, optionally, the additional component are added to a mixing vessel and the calcium oxide is added over a period of between about 1 and 60 minutes. With continual agitation, the mixture gradually thickens and passes through a plastic stage and then crumbles to produce the product. In this embodiment the temperature rise is much slower and the final temperature is much lower.

In yet another embodiment, in a continuous process, glycerol and, optionally, the additional component and calcium oxide are added to a reaction vessel in separate streams and the product is periodically removed from the reaction vessel at intervals of between about 1 and 60 minutes so that an approximately constant level of product is maintained in the reaction vessel. In a variation of this process, the glycerol and calcium oxide are rapidly premixed, as described above, prior to addition to the reaction vessel. In a further variation of this process, a portion of the product is recycled back into the reaction vessel on a continuous basis.

In a further variation of this process, the additional component may be added in a separate stream and not combined with the glycerol.

According to another aspect of the invention, there is provided a glycerol derived material produced by a method as hereinbefore described.

According to another aspect of the invention, there is provided an animal feedstuff or animal feedstuff additive produced by a method as hereinbefore described.

According to another aspect of the invention, there is provided a method of producing a calcium salt of glycerol the method including the steps of combining glycerol with a metal oxide, the glycerol having a water content of between about 5% and 50%, and the rate of combination of the glycerol and the metal oxide and the amount of the metal oxide being selected so that at least part of the water present in the glycerol reacts with the metal oxide and at least part is driven off by heat produced in the exothermic reaction to produce the calcium salt of glycerol in the form of a solid product.

The calcium salt may be a glyceroxide such as calcium monoglyceroxide, calcium diglyceroxide or tricalcium octaglyceroxide or a combination of these depending on the reaction conditions as described and discussed in representative Examples 1-8.

The method of the invention can thus be carried out according to four Process Types. These are set out in further detail below.

Process Type 1: Batch Mixing

In different embodiments of Process Type 1, vessels were those designed for viscous mixtures, such as ribbon-mixers, dough-mixers, z-blade mixers, kneaders and those suitable for heavy duty applications.

A predetermined quantity of glycerol of known composition and, optionally, an additional component as described above, was charged into a mixing vessel. With the agitator running, a predetermined quantity of quicklime was slowly added over a period of 1-60 minutes. There was a relatively low rate of increase in the temperature and the expansion of the reaction mixture. With continual agitation, the mixture gradually thickened and went through a plastic stage. The mixture then crumbled, to resemble a flaky short-pastry dough, and evolution of steam took place. The container could then be emptied and the product broken up and packed into suitable moisture-free bags.

Process Type 2: Rapid Charging, Rapid Mixing, Rapid Discharge

In Process Type 2, a predetermined quantity of glycerol of known composition and, optionally, an additional component as described above, obtained as a by-product in the production of bio-diesel was charged into a suitable mixing vessel.

With the agitator running, a predetermined amount of quicklime was rapidly added over a period of 1-10 seconds and the mixture was agitated for a further period of 1-30 seconds. The temperature rose rapidly and the reaction mixture expanded.

The mixture was then discharged rapidly (over a period of 1-60 seconds) into a suitable container and allowed to stand. The reaction continued with the accompanying evolution of water and the mixture became plastic with a gummy constituency. The product then began to crumble. In different runs, the crumbling stage was reached over a period of between about five minutes and an hour.

One of the limitations of this method was the rapidity of the temperature rise, which resulted in some loss of glycerol, which was probably trapped in the steam and volatile products produced in the reaction. In some embodiments of this method it was found that discharging the product before it began to solidify could be difficult.

Process Type 3: Continuous Mixing

In Process Type 3, a predetermined quantity of the product produced as described in Process Types 1 and 2 was charged into a suitable mixing vessel. The product was agitated and pre-determined amounts of glycerol and quicklime were added. In different embodiments of the intention, the quicklime and glycerol were fed either in separate streams or rapidly premixed (as described in Process Type 1) on a batch or continuous basis, prior to addition to the mixer.

Product was regularly removed from the mixer for dressing and bagging, whilst an approximately constant level of product was retained in the mixer. This process effectively produced a dry bed of finished or semi-finished material over which the fresh reactants were spread.

In a different embodiment of this method continuous discharge ribbon blenders, plough-mills, plough-shear mills, pug mills, Littleford mixers and Lodige mixers were all found to be suitable.

Process Type 4: Continuous Mixing with a Recycle of Product

In Process Type 4, a portion of the product was continuously returned back to the mixer. One or more of the raw materials could then be pre-mixed, prior to entry into the mixer. In a variation on this embodiment of the invention, the raw materials were added adjacent to the return mixer feed.

In each of the Process Types described above, provision was made for the escape of steam and volatiles from the mixture. The solid products were deliquescent in some instances depending on product composition and needed to be packaged, immediately after production, in moisture-proof packaging. The glycerol derived materials were in some instances depending on the specific process conditions utilised and which dictated the resulting chemical composition of the solid products found to be hygroscopic materials which, on exposure to humid air, slowly reabsorbed moisture and could become sticky over time (Table 1). The pH was typically between about 9 and 13.

The invention is now described, by way of example of batch processes with reference to the following Examples.

EXAMPLE 1

Experimental Procedure

A commercial grade of semi-refined, wet glycerol (300.16 g; glycerol, 80.8% (w/w); water, 13% (w/w); methanol, 0.5% (w/w) max; sodium, 2% (w/w max); ash, 7.5% (w/w) max) was charged into an open, non-metal mixing vessel (i.e. prone to heat/moisture loss) and agitated at room temperature. With the agitator running, quicklime (83.00 g; calcium oxide, 94% (w/w): calcium carbonate, 3.9% (w/w); magnesium oxide, 0.5% (w/w)) was added in one portion in less than 1 minute. The temperature of the mixture changed as follows:
  0 min (before addition): 18.7° C.
  1 min after addition: 36.3° C.
  2 min after addition: 56.6° C.
  3 min after addition: 81.1° C.
  4 min after addition: 91.1° C. (max)
  7 min after addition: 70.7° C.

During the 7 minute period the mixture gradually thickened and went through a plastic stage and then crumbled to resemble a flake-like, short-pastry dough. Evolution of steam from the hot material took place. The damp light brown coloured granular material was spread out in an open plastic container and allowed to dry. The resulting cream coloured material was separated using sieves into particle sizes of <1.4 mm, 1.4-2.8 mm and >2.8 mm, respectively. The three fractions were stored in sealed containers.

Chemical Analysis
Fraction 1 (<1.4 mm)
  Glycerol (ex diglyceroxide): 64.9% (w/w)—Method: titrimetric
  Calcium: 16.2% (w/w)—Method: titrimetric
  Free water: 9.2% (w/w)—Method: Karl Fischer
  pH (1% w/w suspension in distilled water): 12.1
Fraction 2 (1.4-2.8 mm)
  Glycerol (ex diglyceroxide): 64.2% (w/w)—Method: titrimetric
  Calcium: 16.1% (w/w)—Method: titrimetric
  Free water: 8.1% (w/w)—Method: Karl Fischer
  pH (1% w/w suspension in distilled water): 11.9
Fraction 3 (>2.8 mm)
  Glycerol (ex diglyceroxide): 63.7% (w/w)—Method: titrimetric
  Calcium: 15.8% (w/w)—Method: titrimetric
  Sodium: 2.2% (w/w)—Method: AAS
  Free water: 4.6% (w/w)—Method: Karl Fischer
  pH (1% w/w suspension in distilled water): 12.0

Fraction 1 was analysed in duplicate in an independent laboratory in the United Kingdom as follows:
Fraction 1 (<1.4 mm)
  Glycerol (ex diglyceroxide): 67.5% (w/w)—Method: USP (HPLC)
  Calcium: 16.2% (w/w)—Method EP 2.5.11
  Free water: 5.2% (w/w)—Method: USP LOD
  pH (1% w/w in distilled water): 12.1

X-Ray Diffraction (XRD)
Method

The sample was split and a representative portion was analysed by X-ray diffraction (XRD) to obtain its bulk phase assemblage. A Siemens D500 diffractometer was used, with a step size of 0.02° 2θ and a counting time of 1 second per step applied over a range of 5 to 80° 2θ. The method made use of the net intensity of the main peaks of the phases, and identification was based on the crystal structure of crystalline phases (i.e. not those that are amorphous to XRD), and occur in amounts more than ~3 to 4 mass %.

Results

The sample consisted of spherical cream coloured nodules. The predominant phase (>50 mass %) phase was identified as calcium diglyceroxide, with trace amounts (<5 mass %) each of calcium hydroxide and calcium carbonate. This result was confirmed by analysis by an independent analytical laboratory in the Netherlands. The reference pattern in the JCPDS database was of poor quality, but the measured pattern as shown in FIG. 1 matched the diffraction pattern of calcium diglyceroxide recently published by Kouzu et al (Applied catalysis A: General 334 (2008) 357-365).

If a material with an orthorhombic symmetry is assumed with lattice parameters of a=13.506 Å, b=21.286 Å and c=13.347 Å, almost all reflections can be explained by this structure.

High Pressure Liquid Chromatography (HPLC)
Preparation of Samples

The product granules were crushed weighed out (50 mg) in a clean, dry vial, washed with de-ionised water into a volumetric flask, shaken well to fully solubilise the powder, made up to 100 ml and mixed well. The reference and raw material glycerol samples, respectively, were weighed out (50 mg each) in clean, dry vials and washed with de-ionised water into volumetric flasks, made up to 100 ml each and mixed well.

System

A Waters 717 autosampler, 410 refractive index detector and Agilent 1100 pump, controlled with Waters Empower software was used.

Separation was achieved on a Biorad Aminex HPX 87H column at a flow rate of 0.6 ml minute at 65 C. The injection volume was 10 µl.

Eluent
  2 L of 5 mM $H_2SO_4$
  0.5 ml concentrated $H_2SO_4$ in 2 liter MilliQ water
  Filtered under vacuum (0.45 micron filter)

Quantification Results

The starting material glycerol was found to contain 80.8% (w/w) glycerol versus reference standard*

The solubilised product powder was found to contain 67.2% (w/w) glycerol versus reference standard*

*Analytical grade glycerol (>99.9% purity, 0.5 g/liter) was used as glycerol reference standard Gas Chromatography-Mass Spectrometry (GC-MS)
Preparation of Samples The crushed product granules and glycerol reference, respectively, were dissolved in pyridine and derivatised with MSTFA (N-Methyl-N-trimethylsilyl-trifluoroacetamide).

System
  Instrument: Agilent 6890N GC; Agilent 5975 MS (1)
  Column: HP5 (30 m, 0.25 mm ID, 0.25 µm film thickness)
  Instrument Settings
  Injector temperature: 280° C.
  Injection volume: 1 µl Split ratio: 20:1
Constant flow: 1 ml/min
Carrier gas: Helium
MS transfer: 280° C.
EI+; Electron energy 70 eV
Scanning mass range: 40 to 550 m/z
Solvent delay: 8 min
Oven Temperature Program:

| Oven Ramp | ° C./min | Temp (° C.) | Hold (min) |
|---|---|---|---|
| Initial |  | 70 | 0 |
| Ramp 1 | 1 | 76 | 0 |
| Ramp 2 | 8 | 300 | 5 |

Results

The GC-MS spectra of the pyridine extracts of the derivatised analytical grade (>99% w/w) glycerol reference and starting material glycerol showed glycerol (as the trimethylsilyl ether) to be the sole organic compound in the respective samples. No glycerol degradation products or higher order entities were detected under the conditions applied.

Nuclear Magnetic Resonance (NMR) Spectroscopy

System

Varian Inova 400 NMR spectrometer with a $^1$H frequency of 400 MHz and a $^{13}$C frequency of 100 MHz. 5 mm dual broad band PFG probe with a probe temperature of 25° C.

Preparation of Samples

Product granules were transferred to 3 glass vials and crushed to fine powders. NMR solvents (1.5 ml each) were added to the powders to form suspensions with deuterated water and deuterated methanol and a solution in deuterated dimethyl sulfoxide, respectively. The vials were sealed, shaken and left for 30 minutes at room temperature. The NMR solvents were then removed with pasteur pipettes and the respective mixtures filtered through NMR filters (0.45 micron) into 5 mm NMR tubes (clear solutions).

Spectra Recorded

The following spectra were recorded:
Starting Material Glycerol—Reference
Deuterated water ($D_2O$) as solvent—proton and carbon-13 spectra
Deuterated methanol ($CD_3OD$) as solvent—proton and carbon-13 spectra
Deuterated dimethyl sulfoxide (DMSO-$d_6$)—proton and carbon-13 spectra
Extracted Product Powder
Deuterated water ($D_2O$) as solvent—proton and carbon-13 spectra
Deuterated methanol ($CD_3OD$) as solvent—proton and carbon-13 spectra
Deuterated dimethyl sulfoxide (DMSO-$d_6$)—proton and carbon-13 spectra Results The proton and carbon-13 NMR spectra of the filtered reaction product extracts in deuterated water and deuterated methanol, respectively, closely matched the spectra of the starting material glycerol reference standard in these solvents.

The proton spectra of glycerol using deuterated water as NMR solvent were characterised by doublet of doublets patterns at 3.49 ppm (2H) and 3.59 ppm (2H) and multiplet pattern at 3.69-3.74 ppm (1H). The proton spectra of the extracted product granules using deuterated water as NMR solvent were characterised by identical doublet of doublets patterns at 3.46 ppm (2H) and 3.55 ppm (2H) and multiplet pattern at 3.66-3.71 ppm (1H) using the same reference standard.

The proton spectra of glycerol using deuterated methanol as NMR solvent were characterised by doublet of doublets patterns at 3.52 ppm (2H) and 3.60 ppm (2H) and multiplet at 3.66-3.71 ppm (1H). The proton spectra of the extracted product granules using deuterated methanol as NMR solvent were characterised by identical doublet of doublets patterns at 3.52 ppm (2H) and 3.60 ppm (2H) and multiplet at 3.64-3.70 ppm (1H) using the same reference standard.

The carbon-13 spectra of glycerol using deuterated water as NMR solvent were characterised by lines at 63.18 ppm and 72.75 ppm. The carbon-13 spectra of the extracted product granules using deuterated water as NMR solvent were characterised by lines at 63.19 ppm and 72.75 ppm using the same reference standard.

The carbon-13 spectra of glycerol using deuterated methanol as NMR solvent were characterised by lines at 64.13 ppm and 73.61 ppm. The carbon-13 spectra of the extracted product granules using deuterated methanol as NMR solvent were characterised by lines at 64.36 ppm and 73.77 ppm using the same reference standard.

However, with deuterated dimethyl sulfoxide as solvent (which dissolved the solid product) a difference in splitting pattern of the C$\underline{H}$ multiplet at 3.25-3.45 ppm in the proton spectra between that of the reaction product (calcium diglyceroxide) and glycerol reference was observed. The doublet of doublet (dd) patterns observed for the non-equivalent geminal C$\underline{H}_2$ protons at 4.52 ppm and 4.44 ppm (glycerol) and 4.52 ppm and 4.40 ppm (calcium diglyceroxide), respectively, were similar in both instances, with both spectra referenced to the DMSO-$d_6$ peak at 2.50 ppm. The carbon-13 spectra were similar with C$\underline{H}_2$ observed at 63.33 ppm (glycerol) and 63.08 ppm (calcium diglyceroxide) and C$\underline{H}$ at 72.73 ppm (glycerol) and CH at 72.50 ppm (calcium diglyceroxide), respectively, with both spectra referenced to the centre peak of the DMSO-$d_6$ heptet at 39.51 ppm.

This appears to indicate that the solid product (calcium diglyceroxide) decomposed in the deuterated water and deuterated methanol solvents to release glycerol in solution whereas this did not occur in deuterated dimethyl sulfoxide.

Analysis—General Conclusion

XRD analysis of a representative sample of the reaction product showed that the main component of the solid product is calcium diglyceroxide which exists as such in the solid state, but decomposes in water and methanol (deuterated or non-deuterated), respectively, to release the observed glycerol in solution, as observed by NMR, HPLC and GC-MS.

EXAMPLE 2

Experimental Procedure

A metal reactor was charged with a commercial grade of semi-refined, wet glycerol (235 kg; glycerol, 82.49% (w/w); water, 13.17% (w/w); methanol, 0.012% (w/w); salts (NaCl) as ash, 4.15% (w/w); MONG (Matter Organic Not Glycerol), 0.19% (w/w)) and agitated at moderate speed at room temperature (10° C.). Quicklime (65 kg; calcium oxide, 94% (w/w): calcium carbonate, 3.9% (w/w); magnesium oxide, 0.5% (w/w)) was added in portions over ca 6 minutes and the resulting suspension rapidly agitated. The mixture heated up and steam escaped through 2 open ports on the closed reactor. The mixture gradually thickened and about 15 minutes after the quicklime addition, the rotating blades were unable to move the mixture. The reaction mixture was tipped out and the solid material broken up and transferred onto two pre-weighed, open, flat boxes to cool. The total weight of the solid, white product was 290 kg. The product material was stored in sealed bags. The product hardened and consequently had to be milled to form a powder.

It is important to note that, in comparison to the small-scale experiment described in Example 1 wherein an open, non-metal reaction vessel prone to heat and moisture loss wherein a maximum reaction mixture temperature of 91.1 degrees Celsius was reached, the reaction vessel used in this pilot scale experiment was from metal and mostly enclosed (with only a small chimney/port). A high, variable speed 'high shear' mixer with a Cowles blade agitator was used. Compared to Example 1, only a relatively limited heat loss through the chimney, side walls and metal lid of the vessel was possible. The high shear blade eliminated granulation and this resulted in a solid mass, further restricting the loss of heat and moisture. Although the maximum temperature of the reaction mixture could not be measured as the system was not fitted with a temperature probe, it estimated to have reached a substantial higher temperature of between ca 120 degrees Celsius and 140 degrees Celsius compared to the 91.1 degrees Celsius of the reaction mixture described in Example 1.

Chemical Analysis

Glycerol (ex monoglyceroxide): 65.40% (w/w)—Method: titrimetric

Calcium: 15.78% (w/w)—Method: titrimetric

Free water at: 13.31% (w/w)—Method: oven drying

Sodium: 1.41% (w/w)—Method: AAS pH (1% w/w in distilled water): 11.9

The solid product was analysed in duplicate in an independent laboratory in the United Kingdom as follows:

Glycerol (ex monodiglyceroxide): 66.5% (w/w)—Method: USP (HPLC)

Calcium: 15.4% (w/w)—Method EP 2.5.11

Free water: 11.1% (w/w)—Method: USP LOD

X-Ray Diffraction (XRD)

Method

The sample was split and a representative portion was analysed by X-ray diffraction (XRD) to obtain its bulk phase assemblage. A Siemens D500 diffractometer was used, with a step size of 0.02° 2θ and a counting time of 1 second per step applied over a range of 5 to 80° 2θ. The method made use of the net intensity of the main peaks of the phases, and identification was based on the crystal structure of crystalline phases (i.e. not those that are amorphous to XRD), and occur in amounts more than ~3 to 4% (w/w).

Results

XRD analysis showed that the reaction product was similar, but differed in composition from the product obtained in Example 1. The predominant phase (>50 mass %) in this instance was found to be calcium monoglyceroxide, with trace amounts (<5% mass %) each of calcium carbonate and calcium hydroxide.

An experiment was subsequently performed wherein a pure glycerol-water mixture was used as starting material in an appropriate molar ratio (glycerol:calcium oxide=2:1 molar equivalents) and under suitable reaction conditions to produce calcium diglyceroxide in optimal yield and purity with the intention to generate calcium diglyceroxide as reference material and provide material to evaluate in intended applications. The experiment is described in Example 3.

The experiment in Example 3 was repeated with starting materials in different ratios in order to ascertain the effect of relative molar ratios of starting materials on product composition under comparable reaction conditions. The details of these experiments are described in Examples 4-6.

Two control reactions were further performed with calcium oxide and calcium hydroxide, respectively, reacted with dry glycerol. These experiments are described in Examples 7-8.

The results of experiments described in Examples 3-8 are summarised in Table 1.

EXAMPLE 3

Experimental Procedure

A clear, colourless solution (900 g) of glycerol (819.6 g, Sigma Glycerol ReagentPlus ≥99.0% (GC)) and purified water (80.4 g, Chromasolv for HPLC, Sigma-Aldrich), i.e. with glycerol:water molar ratio of 2:1 and weight ratio of ca 91:9 and pH 7 was charged into the stainless steel bowl of a Kenwood kMix food mixer mixing vessel equipped with blade-like agitator (without using the plastic bowl lid with port in order to avoid condensed steam water falling back into the reaction mixture) and agitated at room temperature. With the agitator running, a commercial grade of 94% calcium oxide (265.2 g, 1 molar equivalent) was added in portions over one minute whilst the mixture agitated at maximum speed. An exotherm started after ca 2 minutes and the hot, white suspension thickened gradually to form a dough-like material after ca 5 minutes with steam evolving. The material started breaking up into granules after ca 6 minutes and solid material collected on the reaction vessel. The agitator was stopped after 10 minutes and the solid product left to cool room temperature.

The maximum recorded temperature of the reaction mixture was 116 degrees Celsius starting with a glycerol/water starting material mixture at 23.6 degrees Celcius.

The solid material was transferred to a large glass beaker and sieved to give the following three fractions:

Fraction 1: Free-flowing, white powder, particle size <1 mm (417 g)

Fraction 2: Free-flowing, white granules, particle size 1-2.36 mm (324 g)

Fraction 3: Free-flowing, white granules, particle size >2.36 mm (298 g)

Analysis

A fresh sample of Fraction 1 was analysed in duplicate to give the following mean values:

Glycerol (ex diglyceroxide): 77.2% (w/w)—Method: HPLC

Calcium: 19.1% (w/w)—Method: Alkaline Metals in Foodstuffs by AAS (TM200)

Water: 6.05% (w/w)—Method: Karl Fischer (TM166)

pH (1% suspension in distilled water): 13.2—Method: TM41

The <1 mm particle size fraction (free-flowing powder) prepared in duplicate experiment by the same procedure described in this Example was analysed in duplicate to give the following mean values:

Glycerol (ex diglyceroxide): 72.9% (w/w)—Method: HPLC

Calcium: 18.7% (w/w)—Method: Alkaline Metals in Foodstuffs by AAS (TM200)

Water: 5.84% (w/w)—Method: Karl Fischer (TM166)

pH (1% suspension in distilled water): 13.4—Method: TM41

The 1-2.36 mm particle size fraction (free-flowing granules) prepared in a separate experiment by the same procedure described in this Example was analysed in duplicate to give the following mean values:

Glycerol (ex diglyceroxide): 72.7% (w/w)—Method: HPLC

Calcium: 18.0% (w/w)—Method: Alkaline Metals in Foodstuffs by AAS (TM200)

Water: 6.20% (w/w)—Method: Karl Fischer (TM166)

pH (1% suspension in distilled water): 13.4—Method: TM41

X-ray diffraction analysis (XRD) of Fraction 1 powder confirmed that the material is pure phase calcium diglyceroxide. The diffraction pattern is an identical match of the calcium diglyceroxide pattern published by Kouzu et al for crystalline calcium diglyceroxide which was prepared under anhydrous conditions in refluxing methanol under an inert atmosphere (Kouzou, M.; Applied Catalysis A: General; vol. 334 (2008), page: 357-365).

Hygroscopicity Testing

Weighed samples of fresh Fraction 1 powders and Fraction 2 granules were placed in 100 ml wide-mouth glass bottles open to the air, then re-weighed and physical appearances monitored over time in order to evaluate their tendency to absorb moisture when exposed to the indoor-environment.

The result of the hygroscopicity trial is shown in Table 1.

TABLE 1

| Sample | Particle size | Time | Weight (g) | Weight change from fresh (%) | Physical appearance |
|---|---|---|---|---|---|
| Fraction 1 | <1 mm | Day 0 | 2.85 | | Free-flowing, white powder |
| | | Day 1 | 2.83 | −0.71 | Free-flowing, white powder |
| | | Day 4 | 3.09 | +8.42 | Free-flowing, white powder |
| | | Day 7 | 3.30 | +15.79 | Slightly sticky white powder |
| | | Day 11 | 3.73 | +30.88 | Slightly sticky and white powder |
| | | Day 14 | 3.82 | +34.04 | Sticky and fluffy white powder |
| Fraction 2 | 1-2.36 mm | Day 0 | 2.98 | | Free-flowing, white granules |
| | | Day 1 | 2.92 | −2.05 | Free-flowing, white granules |
| | | Day 4 | 3.14 | +5.37 | Free-flowing, white granules |
| | | Day 7 | 3.30 | +10.74 | Slightly sticky white granules |
| | | Day 11 | 3.63 | +21.81 | Sticky white granules |
| | | Day 14 | 3.71 | +24.49 | Sticky white granules |

A sample of Fraction 1 (<1 mm particle size) powder (ca 7 g) was left in a 250 ml Erlenmeyer flask at the same time and area and has shown little change in physical state over the period. The calcium diglyceroxide granules (1.36 mm particle size) having relatively smaller total exposed surface areas than the corresponding powders (<1 mm particle size) were confirmed to be less hygroscopic for materials treated in the same way. The calcium diglyceroide materials were found to be more tolerant to air exposure than expected taking into account the high solubility of glycerol in water and its hygroscopic nature. These findings are in agreement with the findings of Kouzu et al (Kouzou, M.; Applied Catalysis A: General; vol. 334 (2008), page: 357-365) that calcium diglyceroxide is tolerant to air-exposure.

EXAMPLE 4

Experimental Procedure

The experiment described in Example 3 was repeated on third scale with CaO:Glycerol:Water molar ratio of 2:2:1, i.e. using 2 molar equivalents calcium oxide as opposed to 1 equivalent.

An exotherm started developing after ca 2 minutes and the hot, white suspension thickened gradually to form a white paste after ca 3 minutes with steam evolving. The material started breaking up into granules after ca 4 minutes and solid material collected on the reaction vessel. The agitator was stopped after 5 minutes and the product allowed to cool room temperature to give a white powder (417 g).

Analysis

A fresh sample of the product powder was analysed in duplicate to give the following mean values:

Glycerol (ex glyceroxides): 65.8% (w/w)—Method: HPLC

Calcium: 30.7% (w/w)—Method: Alkaline Metals in Foodstuffs by AAS (TM200)

Water: 8.07% (w/w)—Method: Karl Fischer (TM166)

pH (1% suspension in distilled water): 13.3—Method: TM41

X-ray diffraction analysis (XRD) of the product powder showed that the solid phase consisted of calcium monoglyceroxide, calcium diglyceroxide, tricalcium octaglyceroxide $[Ca_3(C_3H_7O_3)_6.(C_3H_8O_3)_2]$ and calcium hydroxide.

EXAMPLE 5

Experimental Procedure

The experiment described in Example 3 was repeated on third scale with CaO:Glycerol:Water molar ratio of 1:1:1, i.e. using 1 molar equivalent glycerol as opposed to 1 equivalent to ascertain whether the monoglyceroxide would be favoured under these circumstances.

An exotherm started developing after ca 2 minutes and the hot, white suspension thickened gradually to form a white dough-like substance after ca 3 minutes with steam evolving. The material started breaking up into granules at the same time and solid material collected on the reaction vessel. The agitator was stopped after 4 minutes and the product allowed to cool room temperature to give a white powder (435 g).

Analysis

A fresh sample of the product powder was analysed in duplicate to give the following mean values:

Glycerol (ex glyceroxides): 60.6% (w/w)—Method: HPLC

Calcium: 30.0% (w/w)—Method: Alkaline Metals in Foodstuffs by AAS (TM200)

Water: 12.74% (w/w)—Method: Karl Fischer (TM166)

pH (1% suspension in distilled water): 13.2—Method: TM41

X-ray diffraction analysis (XRD) of the product powder showed that the solid phase consisted of calcium monoglyceroxide, calcium diglyceroxide, tricalcium octaglyceroxide $[Ca_3(C_3H_7O_3)_6.(C_3H_8O_3)_2]$ and calcium hydroxide.

EXAMPLE 6

Experimental Procedure

The experiment described in Example 3 was repeated on third scale with CaO:Glycerol:Water molar ratio of 1:2:2, i.e. using 2 molar equivalent water as opposed to 1 molar equivalent (18 wt % as opposed to 9 wt % water with respect to glycerol).

An exotherm started developing after ca 2 minutes and the hot, white suspension thickened gradually to form a white dough-like substance after ca 3 minutes with steam evolving. The material gradually thickened to form a putty-like substance which did not granulate spontaneously. The agitator was stopped after 15 minutes and the solid product allowed to cool room temperature to give a white putty-like white solid (350 g) which could be crumbled into a powder with a spatula.

Analysis

A fresh sample of the product powder was analysed in duplicate to give the following mean values:

Glycerol (ex glyceroxides): 73.7% (w/w)—Method: HPLC

Calcium: 18.1% (w/w)—Method: Alkaline Metals in Foodstuffs by AAS (TM200)

Water: 13.06% (w/w)—Method: Karl Fischer (TM166)

pH (1% suspension in distilled water): 13.2—Method: TM41

The X-ray diffraction (XRD) pattern of a vacuum-dried sample of the product powder was almost identical to that of the product powder in Example 3 and showed that the solid phase consisted of mainly calcium diglyceroxide. Traces of calcium monoglyceroxide and calcium hydroxide were observed in this instance.

This experiment was repeated using a double amount of glycerol, i.e. with a molar ratio of CaO:Glycerol:Water=1:4:2 equivalents. In this instance, however, a thin, pourable paste formed, which solidified to a sticky, semi-solid material on cooling to room temperature. This material was vacuum-dried at room temperature for 2 days, but remained sticky.

EXAMPLE 7

Control Experiment A Prior Art

Experimental Procedure

The experiment described in Example 3 was repeated on third scale with CaO:Glycerol:Water molar ratio of 1:2:0, i.e. under anhydrous conditions to ascertain the exotherm generated in the reaction of the oxide with glycerol.

Addition of calcium oxide to the clear, colourless glycerol-water mixture gave a white suspension, which thickened slightly over the next 3 minutes to form a thin, white paste. The paste remained unchanged and the agitator was stopped after a total reaction time of 20 minutes.

The maximum recorded temperature of the reaction mixture was 26.1 degrees Celsius starting with a glycerol/water starting material mixture at 20.2 degrees Celcius.

The paste solidified on standing overnight to form a putty-like substance, which could be broken up into a powder.

X-ray diffraction (XRD) of the solid phase of a vacuum-dried sample of the product powder showed that it consisted of mainly tricalcium octaglyceroxide $[Ca_3(C_3H_7O_3)_6 \cdot (C_3H_8O_3)_2]$.

This result (Example 7, triglyceroxide predominant at room temperature) agrees with the finding of Fujii et al (K. Fujii, W. Kondo; Calcium glyceroxides formed in the system of calcium oxide-glycerol; Zeitschrift für anorganische and allgemeine Chemie; Volume 359 Issue 5-6, Pages 296-304) reporting that, under anhydrous conditions, the formation of tricalcium octaglyceroxide formation is favoured at room temperature (25 degrees Celsius) over 5 days using a large excess of glycerol with respect to calcium oxide.

EXAMPLE 8

Control Experiment B

Experimental Procedure

The experiment described in Example 7 was repeated with a $Ca(OH)_2$:Glycerol:Water molar ratio of 1:2:0, i.e. under anhydrous conditions using calcium hydroxide instead of calcium oxide to ascertain the exotherm generated in the reaction of the oxide with glycerol relative to the exotherm generated under similar reaction conditions when using the corresponding oxide described in Example 7.

Addition of calcium hydroxide to the clear, colourless glycerol-water mixture (20.5 degrees Celsius) gave white suspension, which thickened slightly over the next 4 minutes to form a light cream-coloured paste. The paste remained unchanged and the agitator was stopped after a total reaction time of 20 minutes.

The maximum recorded temperature of the reaction mixture was 44.2 degrees Celsius starting with a glycerol/water starting material mixture at 20.5 degrees Celcius.

The paste solidified to form a solid block on standing overnight.

X-ray diffraction (XRD) of the solid phase of a vacuum-dried sample of the solidified product showed that it consisted of mainly calcium diglyceroxide. The ratio between the low angle reflections indicated that a minor amount of calcium monoglyceroxide was present.

It is concluded that tricalcium octaglyceroxide formation is favoured when the reaction mixture is at room temperature (26.1 degrees Celsius maximum) under anhydrous conditions with the use of calcium oxide (Example 7), whereas calcium diglyceroxide formation is favoured under the same anhydrous conditions using calcium hydroxide leading to a higher reaction mixture temperature (44.2 degrees Celsius maximum) as the result of the limited exotherm generated under these conditions (Example 8).

Calcium hydroxide appears to be more reactive towards glycerol than calcium oxide when comparing the relative exotherms observed in experiments performed under similar conditions described in Example 7 (temperature rise of 5.9 degrees Celsius reacting 1 molar equivalent calcium oxide with 2 molar equivalents anhydrous glycerol) and Example 8 (temperature rise of 23.7 degrees Celsius reacting 1 molar equivalent calcium hydroxide with 2 molar equivalents anhydrous glycerol). It is therefore concluded that glyceroxide formation occurs mainly via the hydroxide in aqueous medium, e.g. at intermediate temperatures in aqueous medium at intermediate temperature range with a CaO:Glycerol:Water molar ratio of 1:2:1 and 1:2:n equivalents, respectively:

Reactions Occurring in the Presence of 1 Molar Equivalent Water:

$$CaO + H_2O \rightarrow Ca(OH)_2 \quad \quad 1.$$

$$Ca(OH)_2 + 2C_3H_8O_3 \rightarrow Ca(C_3H_7O_3)_2(s) + 2H_2O^* \quad \quad 2.$$

Reactions Occurring in the Presence of Excess (n Equivalents) Water $$CaO + nH_2O \rightarrow Ca(OH)_2 + (n-1)H_2O* \qquad 1.$$

$$Ca(OH)_2 + 2C_3H_8O_3 \rightarrow Ca(C_3H_7O_3)_2(s) + 2H_2O* \qquad 2.$$

* The amount of water removed from the system as steam is related to the amount of heat generated though the exothermic reaction of the metal oxide with water and to a lesser extent the smaller amount of heat generated by the exothermic reaction of the formed hydroxide with glycerol. The amount of heat formed and available throughout the process to generate and drive off steam is determined by factors including but not limited to the design (open versus closed) and material of construction of the reactor (well insulated versus not insulated), the speed and method of mixing/agitation, the particle size and tempo of addition of the metal oxide to the glycerol-water mixture, the relative amount of water present, the reaction mixture volume/scale and pressure.

Fujii et al (K. Fujii, W. Kondo; Calcium glyceroxides formed in the system of calcium oxide-glycerol; Zeitschrift für anorganische and allgemeine Chemie; Volume 359 Issue 5-6, Pages 296-304) reported that, under anhydrous conditions, diglyceroxide formation was found to be favoured at intermediate temperatures (75-85 degrees Celsius heating for 5 days), the monoglyceroxide at high temperatures (120-130 degrees Celsius heating for 3-4 days) and the calcium hexaglyceroxide at low temperatures (10-15 degrees Celsius).

These findings correlate with the trend of glyceroxides species versus temperature found to form in aqueous medium with CaO:Glycerol molar ratios of 1:2 in open food mixers (Examples 1, 3, 5 & 6 performed at moderate temperatures i.e. maximum 91-116 degrees Celsius—diglyceroxide predominant) versus closed metal reactor (Example 2 performed at the highest temperature, estimated ca 120-140 degrees Celsius)—monoglyceroxide predominant). Examples 4 & 5, wherein a molar excess of calcium oxide was used with respect to glycerol, did not follow the same trend, as expected.

The fast reaction of the metal oxide with water appears to be under kinetic control with the slower, secondary reaction of the hydroxide with glycerol under thermodynamic control favouring formation of the glyceroxide specie in the lowest energy, most stable state possible at given reaction conditions.

Reaction conditions can therefore be selected to prepare the glyceroxide of choice, e.g. calcium monoglyceroxide (high temperature, highest energy configuration, least stable) versus calcium diglyceroxide (intermediate temperature, intermediate energy configuration) versus tricalcium octaglyceroxide (room temperature, lowest energy configuration, most stable).

The results of the experiments described in Examples 1-8 are summarised in Table 2.

TABLE 2

| Example | Molar ratio CaO | Molar ratio Glycerol | Molar ratio Water | Temperature[1] | Scale (glycerol + water) | Product appearance | Product composition[4] |
|---|---|---|---|---|---|---|---|
| 1 | 1 | 1.9 | 1.6 | Intermediate (max 91° C.) | 300 g | Solid | Calcium monoglyceroxide |
| 2 | 1 | 1.9 | 1.6 | High (est ca 120-140)[3] | 235 kg | Solid | Calcium diglyceroxide |
| 3 | 1 | 2 | 1 | Intermediate (max 116° C.) | 900 g | Solid | Calcium diglyceroxide |
| 4 | 2 | 9 | 1 | Intermediate | 300 g | Solid | calcium monoglyceroxide, calcium diglyceroxide, tricalcium octaglyceroxide and calcium hydroxide |
| 5 | 1 | 1 | 1 | Intermediate | 300 g | Solid | calcium monoglyceroxide, calcium diglyceroxide, tricalcium octaglyceroxide and calcium hydroxide |
| 6 | 1 | 2 | 2 | Intermediate | 300 g | Solid | Calcium diglyceroxide |
| N/A | 1 | 4 | 2 | Intermediate | 300 g | Semi-solid | N/A |
| 7 | 1 | 2 | 0 | Low (max 26.1° C.) | 300 g | Thin paste, solidified overnight | Tricalcium octaglyceroxide |
| 8 | 1[2] | 9 | 0 | Low-intermediate (max 44.2° C.) | 300 g | Paste, solidified overnight | Calcium diglyceroxide |

[1] Relative maximum reaction mixture temperature
[2] Calcium hydroxide used instead of calcium oxide
[3] Estimated in closed pilot plant metal reactor, refer to discussion (Example 2)
[4] Main components as determined by X-ray diffraction analysis of the solid phases The utilisation of inorganic acids as additives is now described, by way of example with reference to Examples 9 to 20.

The effect of added concentrated inorganic acids (phosphoric acid, hydrochloric acid and sulphuric acid) in molar ratios ranging from 0.001 to 2 equivalents with respect to the metal oxide (1 molar equivalent), water (1 molar equivalent)

and glycerol (2 molar equivalents) on the observed exotherm in each instance in the reaction of calcium oxide with wet glycerol in a small scale series is illustrated in Example 9.

EXAMPLE 9

Experimental Procedure

A series of small scale reactions were performed to establish the relative exotherms and visual observations when adding calcium oxide to glycerol-water mixtures acidified with various amounts of concentrated phosphoric acid, hydrochloric acid and sulphuric acid, respectively to glycerol-water mixtures relative to acid free controls and also to select the most promising candidates which would be suitable for scale-up and further evaluation.

Well-mixed stock solutions (300 g each) of glycerol (273.2 g, Sigma Glycerol ReagentPlus ≥99.0% (GC)) and purified water (26.8 g, Chromasolv for HPLC), i.e. with a glycerol:water molar ratio of 2:1 equivalents and weight ratio of ca 91:9 were prepared.

A commercial grade of 94% calcium oxide (8.84 g each, 94% CaO) was added to the glycerol-water mixture (30.0 g or 150 each) which were acidified using different amounts of inorganic acid ranging from 0.001 to 2 molar equivalents in open 250 ml glass beakers, the mixtures stirred (magnetic stirrer bar) and temperatures recorded. Molar ratios, observations and temperatures are depicted in Table 3.

TABLE 3

| | M[6] | | | Acid | | | | T & PS[2] | | | | | |
|---|---|---|---|---|---|---|---|---|---|---|---|---|---|
| G[4] | W[5] | CaO | Acid | added | Scale[3] | pH[7] | 0 min[1] | 1 min | 2 min | 3 min | 4 min | 5 min | |
| 2 | 1 | 1 | 0 | None (control) | 30 g | 7 | 21.5 | 23.5 susp | 28.2 susp | 75.5 paste | 66.8 paste | 64.2 paste | |
| 2 | 1 | 1 | 9 | $H_3PO_4$ | 30 g | 1 | 34.8 | 115 susp/foam | 120[8] susp/foam | 98.7 susp | 88.1 susp | 78.8 susp | |
| | | | | | | | 0.5 min | 1.5 min | 2.5 min | 3.5 min | 4.5 min | | |
| | | | | | | | 97.8 susp/foam | 119 susp/foam | 116 susp | 91.7 susp | 80.9 susp | | |
| 2 | 1 | 1 | 1 | $H_3PO_4$ | 30 g | 1 | 34.2 | 93.0 susp/foam | 119[8] susp/foam | 107 susp | 85.9 susp | 75.7 susp |
| | | | | | | | 0.5 min | 1.5 min | 2.5 min | 3.5 min | 4.5 min | | |
| | | | | | | | 89.9 susp/foam | 115 susp/foam | 110 susp | 92.0 susp | 80.1 susp | | |
| 2 | 1 | 2 | 1 | $H_3PO_4$ | 30 g | 1 | 29.5 | 138 solid | 141 Solid[9] | solid | solid | solid |
| | | | | | | | 0.5 min | 1.5 min | | | | | |
| | | | | | | | 110 paste/foam | 140 solid | | | | | |
| 2 | 1 | 1 | 0.1 | $H_3PO_4$ | 30 g | 1 | 23.4 | 39.6 susp | 36.3 susp | 33.7 susp | 32.1 susp | 30.9 susp |
| 2 | 1 | 1 | 0.01 | $H_3PO_4$ | 30 g | 1-2 | 22.5 | 25.6 susp | 25.7 susp | 25.4 susp | 25.2 susp | 25.0 susp |
| 2 | 1 | 1 | 0.01 | $H_3PO_4$ | 30 g | 3[10] | 24.0 | 25.9 susp | 26.8 susp | 26.9 susp | 26.9 susp | 27.0 susp |
| 2 | 1 | 1 | 0.01 | $H_3PO_4$ | 30 g | 4-5[11] | 25.0 | 26.3 susp | 27.5 susp | 27.8 susp | 27.9 susp | 27.9 Susp |
| | | | | | | | | | | | | 10.0 min | |
| | | | | | | | | | | | | 28.0 | |
| 2 | 1 | 1 | 0.01 | $H_3PO_4$ | 30 g | 5-6[12] | 25.0 | 27.1 susp | 29.4 susp | 30.9 susp | 32.0 susp | 33.0 susp |
| | | | | | | | | | | | | 10.0 min | |
| 2 | 1 | 1 | 0.01 | $H_3PO_4$ | 30 g | 10[13] | 25.5 | 65.1 paste | 68.2 paste | solid | solid | 60.0 solid |
| | | | | | | | 0.5 min | | | | | | |
| | | | | | | | 68.3 paste | | | | | | |
| 2 | 1 | 1 | 0.005 | $H_3PO_4$ | 150 g | 2 | 21.5 | 25.8 susp | 30.9 susp | 36.5 susp | 44.4 susp | 60.3 susp |
| | | | | | | | 0.5 min | 1.5 min | 2.5 min | 3.5 min | 4.5 min | 8.0 min | |
| | | | | | | | 22.7 susp | 26.2 susp | 31.6 susp | 41.1 susp | 50.7 susp | 125 paste | |
| 2 | 1 | 1 | 0.001 | $H_3PO_4$ | 150 g | 3-4 | 21.7 | 23.3 susp | 29.0 susp | 85.0 susp | 124 solid | 129 solid |
| | | | | | | | 0.5 min | 1.5 min | 2.5 min | 3.5 min | 4.5 min | 6.0 min | |
| | | | | | | | 22.3 susp | 26.2 susp | 61.2 susp | 99.9 paste | 129 solid | 127 solid | |
| 2 | 1 | 1 | 0 | None (control) | 150 g | 7 | 22.0 | 23.7 susp | 30.7 susp | 88.9 susp | 110 paste | 121 paste |
| | | | | | | | 0.5 min | 1.5 min | 2.5 min | 3.5 min | 4.5 min | 9.0 min | |
| | | | | | | | 22.7 susp | 26.1 susp | 78.3 susp | 94.6 paste | 119 paste | 111 solid | |
| 2 | 1 | 1 | 1 | HCl | 30 g | 1 | 33.2 | 108 susp/foam | 92.8 susp | 77.7 susp | 66.5 susp | 58.1 susp |
| | | | | | | | 0.5 min | 1.5 min | 2.5 min | 3.5 min | 4.5 min | 15.0 min | |
| | | | | | | | min 110[8] susp/foam | 103 susp | 85.5 susp | 72.0 susp | 62.0 susp | 57.0 susp | |

TABLE 3-continued

| G[4] | W[5] | M[6] CaO | Acid | Acid added | Scale[3] | pH[7] | T & PS[2] | | | | | |
|---|---|---|---|---|---|---|---|---|---|---|---|---|
| 2 | 1 | 1 | 0.1 | HCl | 30 g | 1 | 33.1 | 85.0 paste | 82.1 paste | (78.1) solid | solid | solid |
| 2 | 1 | 1 | 0.01 | HCl | 30 g | 1-2 | 30.3 | 81.2 susp | 77.3 paste | (89.7) solid | solid | solid |
| 2 | 1 | 1 | 0.01 | HCl | 150 g | 1-2 | 22.7 | 77.2 susp | 90.5 susp | 105 paste | 115 paste | 115 paste |
| | | | | | | | 0.5 min | 1.5 min | 2.5 min | 3.5 min | 4.5 min | 6.0 min, |
| 2 | 1 | 1 | 0.001 | HCl | 150 g | 2 | 26.1 susp | 86.0 susp | 96.8 susp | 107 paste | 115 paste | 110 solid |
| | | | | | | | 26.4 | 39.1 susp | 99.1 susp | 123 paste | 118 solid | 111 solid |
| | | | | | | | 0.5 min | 1.5 min | 2.5 min | 2.5 Min | 3.5 Min | |
| 2 | 1 | 1 | 1 | $H_2SO_4$ | 30 g | 1 | 31.9 susp | 92.5 susp | 109 paste | 122 paste | 115 solid | |
| | | | | | | | 57.5 | 130 susp/Foam | 135 paste | 129 paste | 119 paste | 109 paste |
| | | | | | | | 0.5 min | 1.5 min | 2.5 min | 3.5 min | 4.5 min | 10 min |
| | | | | | | | 73.5 susp/foam | 141 susp/foam | 134 paste | 122 paste | 113 paste | 65.3 paste |
| 2 | 1 | 1 | 0.1 | $H_2SO_4$ | 30 g | 1 | 29.1 | 77.0 susp | 87.9 paste | 89.9 paste | solid | solid |
| 2 | 1 | 1 | 0.01 | $H_2SO_4$ | 30 g | 1 | 26.8 | 79.7 paste | 72.2 paste | 67.0 paste | 71.7 solid | 77.6 solid |
| 2 | 1 | 1 | 0.001 | $H_2SO_4$ | 150 g | 2 | 23.4 | 82.3 susp | 110 paste | 124 paste | 119 solid | 113 solid |
| | | | | | | | 0.5 min | 1.5 min | 2.5 min | 3.5 min | 4.5 min | |
| | | | | | | | 30.5 susp | 91.1 susp | 121 paste | 123 paste | 115 solid | |

[1] Temperature at point of calcium oxide addition
[2] Temperature and physical state (suspension versus paste versus solid) of the reaction mixture. Temperatures were measured with a temperature probe (<100° C.) and high temperature thermometer (>100° C.)
[3] Glycerol + water (g)
[4] Pharmaceutical grade glycerol
[5] Purified water
[6] Molar ratio
[7] pH of glycerol-water-acid mixtures as measured with lithmus paper (1 hour developing time)
[8] Calcium oxide added in portions over 30 seconds to control the very fast and highly exothermic reaction with large amount of foam formation from ca 0.5 to ca 2 minutes following calcium oxide addition
[9] Fast and highly exothermic reaction with large amount of foam formation. Mixture solidified completely after 2 minutes and reliable temperature readings therefore no longer possible
[10] The pH was increased from 2 to 3 by the addition of calcium hydroxide to the glycerol-water-phosphoric acid solution and the mixture stirred for 10 minutes prior to calcium oxide addition. This did not result in a significant increased in exotherm
[11] The pH was increased from 2 to 4-5 by the addition of calcium hydroxide powder to the glycerol-water-phosphoric acid solution and the mixture stirred for 10 minutes prior to calcium oxide addition. This did not result in a significant increased in exotherm
[12] The pH was increased from 2 to 5-6 by the addition of calcium hydroxide powder to the glycerol-water-phosphoric acid solution and the mixture stirred for 10 minutes prior to calcium oxide addition. This did not result in a significant increased in exotherm initially, but gave an increased maximum temperature of 60° C. after 10 minutes reaction time compared to a maximum of 28° C. reached in the starting pH 4-5 scenario
[13] The pH was increased from 2 to 10 by the addition of calcium hydroxide powder to the glycerol-water-phosphoric acid solution and the mixture stirred for 10 minutes prior to calcium oxide addition. In this instance a fast reaction with high exotherm was observed. The mixture was completely solidified after 3 minutes and reliable temperature readings therefore no longer possible From the small scale reactions summarised in Table 3 it can be seen that the reactions with 1 and 2 molar equivalents, respectively of phosphoric acid added showed the largest and fastest exotherms developing, followed by the acid free reactions, i.e. starting with either neutral solutions or very acidic solutions. However, the addition of small amounts of phosphoric acid of 0.1, 0.01 and 0.005 molar equivalents, respectively, suppressed the exotherm completely of significantly. The addition of only 0.001 molar equivalents was tolerated and resulted in an exotherm of similar rate and magnitude achieved in the comparable acid free reaction on the same scale, leading to faster solid product formation (4 minutes with acid as opposed to 9 minutes without acid). Also refer to the discussion following Example 15 and Table 5 for a discussion of exotherm threshold levels with respect to phosphoric acid dose.

The restoration of exotherm by increasing the pH above 6 by adding calcium hydroxide to the starting solution in the exotherm-inhibited reaction using 0.01 molar equivalents phosphoric acid was furthermore demonstrated.

The reactions with 1 molar equivalent hydrochloric acid and sulphuric acid, respectively, gave similar results, i.e. highly exothermic reactions with foam formation leading to pastes. However, when using 0.1 and 0.01 molar equivalents of these acids, respectively, reduced (as opposed to completely suppressed, in the case of phosphoric acid) exotherms without foam formation and leading to solid product formation were achieved. The reactions with 0.001 molar equivalents hydrochloric acid and sulphuric acid, respectively, gave slightly higher exotherms than that observed in the comparable acid free reaction on the same scale, leading to faster solid product formation (4 minutes with acid as opposed to 9 minutes without acid).

Selected larger scale reactions with phosphoric acid as additive are now described in Examples 10-15.

EXAMPLE 10

Experimental Procedure

A clear, colourless solution (300 g) of glycerol (273.2 g, Sigma Glycerol ReagentPlus ≥99.0% (GC)) and purified water (26.8 g, Chromasolv for HPLC, Sigma-Aldrich), i.e. with glycerol:water molar ratio of 2:1 and weight ratio of ca 91:9 and pH 7 at 21.7 degrees Celsius was charged into the stainless steel bowl of a Kenwood kMix food mixer mixing vessel equipped with blade-like agitator (without using the plastic bowl lid with port in order to avoid condensed steam water falling back into the reaction mixture) and agitated at room temperature. With the agitator running, phosphoric acid (171.5 g, 85% $H_3PO_4$ in water, Sigma-Aldrich) was added slowly and the mixture stirred at room temperature for 5 minutes. A commercial grade of 94% calcium oxide (176.8 g, 2 molar equivalents) was then added to the solution at 32.0 degrees Celsius in portions over 3 minutes to control the exotherm and foam formation whilst the mixture was agitated. A large exotherm was observed after ca 30 seconds with the formation of a light cream coloured slurry and a substantial amount of foam with steam evolving from the very hot mixture, which started to granulate with solid material packing onto the vessel. The agitator was stopped after 3 minutes, the solid material broken up with a spatula and allowed cool to room temperature. The white powdery product (538 g) was then separated by particle size into 2 fractions, i.e. Fraction 1, a free-flowing white powder (222 g) with particle size <1 mm and Fraction 2, free-flowing white granules (316 g) with particle size >1 mm.

Analysis (Fraction 1)
Glycerol: 50.8% (w/w)—Method: HPLC
Calcium: 25.4% (w/w)—Method: Alkaline Metals in Foodstuffs by AAS (TM200)
Phosphorous: 8.2% (w/w)—Method: Metals by ICP-MS (TM201)
Water: 3.71% (w/w)—Method: Karl Fischer (TM166)
pH (1% suspension in distilled water): 12.5—Method: TM41

The powder (Fraction 1) was found to have a similar degree of tolerance to air exposure with respect to the absorption of moisture as found for the calcium diglyceroxide granules (1-2.36 mm particle size) as described in Example 3 (Table 1).

X-ray diffraction analysis (XRD) of Fraction 1 powder has shown that the solid phase consisted of calcium hydrogen phosphate ($CaHPO_4$) and calcium monoglyceroxide (minor). No other known calcium phosphate has been detected.

A series of small scale experiments were subsequently performed in order to ascertain whether the excessive foam formation experienced in a glycerol-water-phosphoric acid-calcium oxide system such as the experiment described in Example 10 could be effectively minimised or eliminated by using blends of calcium oxide and calcium hydroxide in various ratios as opposed to calcium oxide exclusively and hence reducing the relative amount of heat generated in a given period of time under a fixed set of conditions (vessel/mixing/reagent ratio) which would be a function of the oxide dose. It was expected that an exotherm will be generated when reacting the phosphoric acid with the hydroxide, but that the heat generated will be less than in the corrersponding reaction of oxide with the water-phoshoric acid mixture.

This study is described in Example 11.

EXAMPLE 11

Experimental Procedure

A well-mixed stock solution of glycerol (273.2 g, Sigma Glycerol ReagentPlus ≥99.0% (GC)) and purified water (26.3 g, Chromasolv for HPLC), i.e. with a glycerol:water molar ratio of 2:1 and weight ratio of ca 91:9 and phosphoric acid (171.5 g, 85% $H_3PO_4$ in water from Sigma-Aldrich) was prepared, i.e. with a molar ratio of Glycerol:Water:Phosphoric acid=2:1:1 equivalents and 10% of this solution (47.1 g) was used as starting material for each small-scale reaction.

An acid free stock solution was also prepared in a similar way for the use in 3 control experiments in order to compare exotherms relative to the corresponding reactions in the presence of phosphoric acid.

In each small-scale reaction either calcium oxide powder (2 molar equivalents) or calcium hydroxide powder (2 molar equivalents) or a well-mixed blend of calcium oxide and calcium hydroxide powder (2 molar equivalents in total, 1 molar equivalent each) was added quickly in one portion to a stirred solution of the acidic stock solution in a 250 ml glass beaker in each instance and the temperatures and observations recorded as depicted in Table 4.

TABLE 4

| | M[1] | | | | T & PS[2] | | | | | |
|---|---|---|---|---|---|---|---|---|---|---|
| G[3] | W[4] | $H_3PO_4$ | CaO | Ca(OH)$_2$ | 0 min[5] | 1 min | 2 min | 3 min | 4 min | 5 min |
| 2 | 1 | 1 | 9 | 0 | 29.5<br>0.5 min | 138 solid<br>1.5 min | 141 Solid[6] | solid | solid | solid |
| 2 | 1 | 1 | 0 | 2 | 110 paste/<br>foam<br>29.3<br>0.5 min | 140 solid<br>96.4 susp<br>1.5 min | 88.1 paste<br>2.5 min | 77.2 paste<br>3.5 min | 69.9 paste<br>4.5 min | 63.2 paste |
| 2 | 1 | 1 | 1 | 1 | 91.0 susp<br>26.0<br>0.5 min | 93.3 paste<br>120 solid<br>1.5 min | 90.0<br>111C solid<br>2.5 min | 72.5<br>106 solid[7] | 66.3<br>solid | solid |
| 2 | 1 | 1 | 1.5 | 0.5 | 114 paste<br>25.0<br>0.5 min | 118 solid<br>129 solid<br>1.5 min | 108 solid<br>116 solid[8] | solid | solid | solid |
| 2 | 1 | 1 | 0.5 | 1.5 | 104 paste/<br>foam<br>25.2<br>0.5 min | 129 solid<br>112 solid<br>1.5 min | 104 solid<br>2.5 min | solid | solid | solid |
| 2 | 1 | 0 | 2 | 0 | 110<br>22.6<br>0.5 min | 106 solid<br>25.3 susp<br>1.5 min | 91 solid[9]<br>77.8 paste<br>2.5 min | 101 solid<br>3.5 min | solid | solid |
| 2 | 1 | 0 | 0 | 2 | 23.4 susp<br>22.5 | 32.9 susp<br>32.1 paste | 95 solid<br>34.3 paste | 109 solid<br>32.4 paste | 31.1 paste | 30.0 paste |

TABLE 4-continued

| | | M[1] | | | | T & PS[2] | | | |
|---|---|---|---|---|---|---|---|---|---|
| G[3] | W[4] | H₃PO₄ | CaO | Ca(OH)₂ | 0.5 min | 1.5 min | 2.5 min | 3.5 min | 4.5 min |
| 2 | 1 | 0 | 1 | 1 | 26.8 paste | 34.5 paste | 33.5 paste | 31.5 paste | 30.5 paste |
| | | | | | 22.1 | 54.7 paste | 80.6 solid | 79.9 solid | solid |
| | | | | | 0.5 min | 1.5 min | 2.5 min | | |
| | | | | | 32.2 paste | 67.9 solid | 80.0 solid | | |

[1]Molar ratio
[2]Temperature and physical state (suspension versus paste versus solid) of the reaction mixture. Temperatures were measured with a temperature probe (<100° C.) and high temperature thermometer (>100° C.)
[3]Pharmaceutical grade glycerol
[4]Purified water
[5]Temperature at point of calcium oxide and/or calcium hydroxide addition
[6]Fast and highly exothermic reaction with large amount of foam formation. Mixture solidified completely after 2 minutes and reliable temperature readings therefore no longer possible
[7]Significant exotherm with little foam formation. Mixture solidified completely after 3 minutes and reliable temperature readings therefore no longer possible
[8]Fast and highly exothermic reaction with ca half the amount of foam formation observed in comparison to the reaction with calcium oxide exclusively. Mixture solidified completely after 2 minutes and reliable temperature readings therefore no longer possible
[9]Good exotherm with no foam formation. Mixture solidified completely after 3 minutes and reliable temperature readings therefore no longer possible In summary, a trend of decreasing exotherm with decreasing calcium oxide/calcium hydroxide ratio was observed, with corresponding reduced foam formation with reduced exotherm. Foam formation was significantly reduced with a calcium oxide:calcium hydroxide ratio of 1.5:0.5, almost completely eliminated with a calcium oxide:calcium hydroxide ratio of 1:1 and totally eliminated with a oxide:calcium hydroxide ratio of 0.5:1.5.

In the acid free (foam free) control reactions, a good exotherm was observed with the use of calcium oxide, a small exotherm when using calcium hydroxide and an intermediate exotherm when using a calcium oxide:calcium hydroxide blend of 1:1 molar equivalents, as anticipated. This implicates that the reaction temperature and hence associated product favoured at specific temperatures (as discussed in Examples 1-8 and summarised in Table 2) can be controlled, i.e. the process temperature can be effectively lowered and controlled in large scale operations where high temperatures through heat retention in enclosed, metal vessels is more likely by using metal oxide—metal hydroxide blends as opposed to metal oxide exclusively, to favour the formation of a metal diglyceroxide product when using appropriate starting material ratios versus a metal monoglyceroxide (refer to pilot scale Example 2) under acid free conditions.

The effect of replacing the calcium oxide (1 molar equivalent) with a 1:1 mixture of calcium oxide (0.5 molar equivalent) and calcium hydroxide (0.5 molar equivalent) in the absence and presence, respectively, of phosphoric acid (1 molar equivalent) is demonstrated larger scale experiments as described in Examples 12-13.

EXAMPLE 12

The experiment described in Example 10 was repeated using a blend of calcium oxide (0.5 molar equivalents) and calcium hydroxide (1.5 molar equivalents). In this instance a cream coloured putty-like solid (578 g) was obtained in a reaction time of 15 minutes. The solid product hardened at room temperature and could be broken into a powder.

X-ray diffraction analysis (XRD) of the powder has shown that the solid phase consisted of mainly calcium hydrogen phosphate ($CaHPO_4$) with only traces of calcium diglyceroxide. No other known calcium phosphate has been detected.

It is therefore concluded that the lower temperature conditions in this experiment in comparison to the experiment described in Example 10 has resulted in the complete elimination of calcium monoglyceroxide formation and favoured the formation of calcium diglyceroxide which formed in only very limited quantities in relation to the main solid component, calcium hydrogen phosphate.

EXAMPLE 13

The experiment described in Example 10 was repeated using a blend of equal molar equivalents of calcium oxide (1 molar equivalent) and calcium hydroxide (1 molar equivalent). In this instance a granular cream coloured solid (555 g) was obtained in a total reaction time of 4 minutes.

X-ray diffraction analysis (XRD) of the powder has shown that the solid phase consisted of mainly calcium hydrogen phosphate ($CaHPO_4$) with only traces of either calcium monoglyceroxide or calcium diglyceroxide or possibly a mixture of the two. No other known calcium phosphate has been detected.

The larger scale experiments described in Examples 12 and 13 following the initial small scale experiments described in Example 11 have therefore confirmed that the use of blends of calcium oxides and calcium hydroxide as opposed to calcium oxide exclusively facilitates improved reaction control and elimination or reduction of foam formation with obvious potential benefit on especially large scale operations.

EXAMPLE 14

The experiment in Example 10 was repeated with double the amount of water (2 molar equivalents, ca 18% w/w) in the starting glycerol-water mixture. In this instance similar visual observations were made and the agitator also stopped after 3 minutes, the solid material broken up with a spatula and allowed cool to room temperature. The white powdery product (550 g) was then separated by particle size into 2 fractions, i.e. Fraction 1, a free-flowing white powder (227 g) with particle size <1 mm and Fraction 2, white granules (323 g) with particle size >1 mm.

Analysis
Glycerol: 49.4% (w/w)—Method: HPLC
Calcium: 23.7% (w/w)—Method: Alkaline Metals in Foodstuffs by AAS (TM200)

Phosphorous: 7.1% (w/w)—Method: Metals by ICP-MS (TM201)

Water: 5.93% (w/w)—Method: Karl Fischer (TM166)

pH (1% suspension in distilled water): 12.5—Method: TM41

The powder (Fraction 1) was found to have a similar degree of tolerance to air exposure with respect to the absorption of moisture as found for calcium diglyceroxide granules (1-2.36 mm particle size) in Example 3 (Table 1).

X-ray diffraction analysis (XRD) of Fraction 1 powder has shown that the solid phase consisted of mainly calcium hydrogen phosphate ($CaHPO_4$) with no detectable amount of calcium glyceroxides or other known calcium phosphates. All reflections were ascribed to Monetite (calcium hydrogen phosphate), except for one weak, unidentified reflection at $2\theta=22.9°$. It is however very unlikely to be a glyceroxide relection, since all the strong reflections of the glyceroxides described earlier were absent.

The experiment described in Example 10 was repeated with the use of double the amount of phosphoric acid, i.e. 2 molar equivalents as opposed to 1 molar equivalent). In this instance a white, sticky, putty-like material formed.

The experiment described in Example 10 was repeated with the use of a reduced amount of calcium oxide, i.e. 1.5 molar equivalents as opposed to 2 molar equivalents. In this instance a pourable white slurry formed.

The experiment described in Example 10 was repeated with the use of increased amounts of glycerol and water, i.e. 3 molar equivalents glycerol (as opposed to 2 equivalents) and double amount of water, i.e. 2 molar equivalents as opposed to 1 equivalent. In this instance a white, rubbery, putty-like material formed.

The experiment described in Example 10 was repeated with the use of an increased amount of phosphoric acid, i.e. 1.5 molar equivalents phosphoric acid (as opposed to 1 equivalent). In this instance a pourable white paste formed.

EXAMPLE 15

The experiment described in Example 10 was repeated with the use of decreased amounts of both calcium oxide and phosphoric acid relative to glycerol, i.e. 1 molar equivalent calcium oxide (as opposed to 2 equivalent) and 0.5 molar equivalents phosphoric acid (as opposed to 1 equivalent). In this instance a white suspension formed with calcium oxide addition, which quickly heated with foam formation. The suspension gradually thickened over the next 30 minutes to form a white paste. Most of the paste was removed by pouring and stored in an air-tight amber glass bottle where it solidified overnight to form a white, waxy material. A sample of the solid was dried under vacuum for 2 days to give a white powder.

XRD analysis of the vacuum dried powder has shown that the soli9d phase consisted of almost pure calcium hydrogen phosphate with only traces of calcium diglyceroxide. No other known calcium phosphate has been detected.

The experiment described in Example 15 was repeated using a reduced amount of phosphoric acid, i.e. 0.1 molar equivalents as opposed to 0.5 equivalents in order to ascertain whether a solid product could be made by adding less acid. In this instance a complete suppression of exotherm with a maximum temperature of 34.2 degrees Celsius was observed, which confirmed the observation in the corresponding small scale reaction in Example 9 (Table 3).

Decreasing the phosphoric acid amount further to 0.05 molar equivalents gave a similar result (white suspension, 31.0 degrees maximum) as did acidifying with 0.01 molar equivalents (white suspension, 26.0 degrees Celsius maximum), which confirmed the observation in the corresponding small scale reaction in Example 9 (Table 3).

Decreasing the phosphoric acid amount further to 0.002 molar equivalents gave a substantial exotherm with little foam formation leading to a sticky, white powder product.

The experiment described in Example 15 was repeated using 1 and 2 molar equivalents phosphoric acid, respectively as opposed to 0.5 equivalents to ascertain whether the higher exotherm would lead to solid product formation over a longer reaction time as initially allowed in the corresponding small scale reactions in Example 9 (Table 3).

It was confirmed that the use of 2 equivalents phosphoric acid does not give a solid product, even after 30 minutes reaction time. In this instance a very potent exotherm with large amount of foam was observed to give a pourable, white paste, which did not solidify with cooling. A sample of the material was dried under vacuum, but the resulting wet, sticky material was not suitable for XRD analysis.

It was further confirmed that the use of 1 equivalent phosphoric acid does not give a solid product, also after 30 minutes reaction time. In this instance a very potent exotherm with a reduced amount of foam was observed to give a thick, white paste, which became cream-like on cooling overnight. A sample of the material was dried under vacuum, but the resulting cream was not suitable for XRD analysis.

Taking into account the small-scale reactions illustrated in Example 9 (Table 3) using 0.001 molar equivalents phosphoric acid, the "exotherm tolerance level" of phosphoric acid in a CaO:Glycerol:Water:Phosphoric acid=1:2:1:X molar ratio system was found to fall on the lower end between X=0.002 and lower (exotherm) and X=0.01 and higher (no exotherm, Examples 9 & 13) phosphoric acid.

The "exotherm tolerance level" of phosphoric acid in a CaO:Glycerol:Water:Phosphoric acid=1:2:1:X molar ratio system was found to fall on the higher end between X=0.1 (low exotherm, Example 13) and 0.5 (exotherm, Example 12) molar equivalents.

Based on these findings, the observed exotherm trend for a CaO:Glycerol:Water:Phosphoric acid=1:2:1:X molar ratio system when adding the acid to the acidified glycerol-water solution is summarised in Table 5.

TABLE 5

| Molar ratio | | | | Exotherm |
| --- | --- | --- | --- | --- |
| CaO | Glycerol | Water | Phosphoric Acid | Exotherm (Y/N) |
| 1 | 2 | 1 | 2 | Y |
| 1 | 2 | 1 | 1 | Y |
| 1 | 2 | 1 | 0.5 | Y |
| 1 | 2 | 2 | 0.1 | N |
| 1 | 2 | 1 | 0.05 | N |
| 1 | 2 | 1 | 0.01 | N |
| 1 | 2 | 1 | 0.002 | Y |
| 1 | 2 | 1 | 0.001 | Y |

A further series of experiments were performed at this stage in order to investigate the viability of alternative addition sequences using phosphoric acid as additive.

The experiment described in Example 15 was subsequently repeated with phosphoric acid added over 1 minute to the hot calcium oxide-water-glycerol suspension in an attempt to avoid or reduce foam formation as opposed to calcium oxide added to the acidified glycerol-water mixture. In this instance the mixture quickly expanded with substantial foam formation and steam evolving. The resulting hot suspension gradually thickened to form a putty-like paste which again failed to granulate or break up over 30 minutes. The product solidified overnight to form a white, wax-like material.

The experiment described in Example 15 was subsequently repeated using an increased amount of phosphoric acid, i.e. 2 molar equivalents as opposed to 0.5 equivalents. In this instance a white paste formed which was dried under vacuum for 2 days but remained paste-like and not suitable for XRD analysis. Reducing the amount of glycerol and water by half in relation to calcium oxide in this experiment, i.e. with a molar ratio of CaO:Glycerol:Water:Phosphoric acid=1:1: 0.5:2 equivalents, gave a sticky, white, toffee-like paste which solidified to form a putty-like substance. A sample was dried under vacuum for 2 days to give a sticky white material which was not suitable for XRD analysis. Reducing the phosphoric acid dose by half in this instance, i.e. using a molar ratio of CaO:Glycerol:Water:Phosphoric acid=1:1:0.5:1 equivalents, also gave a sticky, white toffee-like paste which hardened with standing to form a hard, putty-like material.

When this experiment was repeated using an alternative adding sequence, i.e. adding the glycerol-water mixture to a hot suspension of calcium oxide and phosphoric acid and thus "coating" the calcium phosphate with glycerol, a thick, sticky white paste which solidified on standing to give a white, toffee-like material, which was not suitable for XRD analysis, even after 2 days vacuum drying. Repeating this experiment with halved amounts of glycerol and water in this instance, i.e. using a molar ratio of CaO:Glycerol:Water:Phosphoric acid=1:0.5:0.25:1 (=4:2:1:4), produced a "putty ball" which could be broken into smaller pieces after cooling. (XRD data not available)

The experiment described in Example 15 was then repeated with a slightly increased amount of phosphoric acid, i.e. 0.75 molar equivalents as opposed to 0.5 equivalents. In this instance a pourable light-brown paste formed, which solidified on cooling to give a wax-like, white solid material. A sample of the solid was dried under vacuum for 2 days to give a white powder.

Experiments utilising hydrochloric acid as additive are described in Examples 16-20.

EXAMPLE 16

This experiment was performed to ascertain the effect of hydrochloric acid addition (0.1 molar equivalents) on the composition and physical state of the product. A higher and quicker exotherm in comparison to the acid free reaction was expected as observed in the preliminary small scale trial series discussed in Example 9 and summarised in Table 3.

Experimental Procedure

A clear, colourless solution (300 g) of glycerol (273.2 g, Sigma Glycerol ReagentPlus ≥99.0% (GC)) and purified water (26.8 g, Chromasolv for HPLC, Sigma-Aldrich), i.e. with glycerol:water molar ratio of 2:1 and weight ratio of ca 91:9 and pH 7 at 21.7 degrees Celsius was charged into the stainless steel bowl of a Kenwood kMix food mixer mixing vessel equipped with blade-like agitator (without using the plastic bowl lid with port in order to avoid condensed steam water falling back into the reaction mixture) and agitated at room temperature. With the agitator running, concentrated hydrochloric acid (14.78 g, 12M, Sigma-Aldrich, 95%) was added slowly and the mixture stirred at room temperature for 5 minutes. A commercial grade of 94% calcium oxide (88.4 g, 1 molar equivalent) was then added to the solution (pH 1) at 23.9 degrees Celsius in portions over 1 minute whilst the resulting hot suspension was agitated. The suspension thickened to a paste after ca 5 minutes which solidified over the next 4 minutes to produce a solid material which was left to cool to room temperature and then broken into a cream coloured powder (356 g).

XRD analysis of the powder showed that the solid phase consisted of mainly calcium diglyceroxide. However, the material was not phase pure calcium diglyceroxide, but also contained a small amount of calcium monoglyceroxide. This is based mainly on the peak ratio of the low angle reflections. For purer diglyceroxide the reflection at $2\theta=8.3°$ appears to the strongest, while here the reflection at $2\theta=10.2°$ is the strongest, indicating the presence of a non negligible amount of calcium monoglyceroxide.

This result is not surprising, as a higher temperature favouring the monoglyceroxide above the diglyceroxide (refer to Table 2) is achieved in the presence of 0.1 molar equivalents hydrochloric acid compared to the corresponding acid free reaction performed under similar conditions on the same scale (refer to Table 3).

EXAMPLE 17

The experiment described in Example 16 was subsequently repeated using a ten-fold increase in hydrochloric acid dose, i.e. one molar equivalent hydrochloric acid as opposed to 0.1 equivalents in order to ascertain the effect on the composition and physical state of the product.

In this instance the calcium oxide was added slowly in portions over 3 minutes to the acidified glycerol-water mixture at 33.5 degrees Celsius to control the high exotherm and foam formation. A hot (boiling), foaming suspension formed which gradually thickened and cooled over 30 minutes. The paste did not break up, granulate or solidify. The cream coloured paste (443 g) had a pleasant smell and could be crumbled into rubbery granules on cooling. Vacuum-drying produced a white powder.

The composition of the vacuum dried powder could not be established by XRD analysis as no matching patterns have been found. None of the known glyceroxides were detected. The measured pattern also did not match that of calcium chloride, various types of hydrated calcium chloride, calcium oxychloride, calcium oxide, peroxide and carbonate.

EXAMPLE 18

The experiment described in Example 16 was subsequently repeated with double the calcium oxide dose, i.e. 2 molar equivalent calcium oxide as opposed to 1 equivalent in order to ascertain the effect on the composition and physical state of the product.

In this instance the calcium oxide was added slowly in portions over 4 minutes to the acidified glycerol-water mixture at 31.6 degrees Celsius to control the high exotherm and foam formation. A hot (boiling), foaming suspension formed which gradually thickened and cooled over 30 minutes. The paste did not break up, granulate or solidify. The resulting thick, rubbery material turned rock solid on standing.

XRD analysis of a powderised sample of the solid material showed that the solid phase consisted of mainly calcium hydroxide. However, one reflection of a different phase was observed. The broad peak at 8.5° indicated the presence of an additional phase, which had at least one dimension with a size in the range of 4-10 nm. The broadness of the reflection indicated that the crystallites are very small. Based on this single peak, identification of this phase was very difficult. It was however likely that this peak was due to the presence of nano-crystals of either calcium monoglyceroxide or calcium diglyceroxide.

EXAMPLE 19

The experiment described in Example 16 was subsequently repeated with half the amount of glycerol, I.e. molar equivalent glycerol as opposed to 2 equivalents in order to ascertain the effect on the composition and physical state of the product.

In this instance the calcium oxide was added in portions over 1 minute to the acidified glycerol-water mixture at 24.9 degrees Celsius. A hot (boiling) suspension formed which gradually thickened to a paste in ca 4 minutes. The paste granulated and solid material collected on the vessel. The agitator was stopped after 7 minutes and the solid product left to cool to room temperature to give a mixture of cream coloured granules and powder (456 g).

XRD analysis of a sample of the product powder showed that the solid phase consisted of mainly calcium hydroxide with minor amounts of both calcium monoglyceroxide and calcium diglyceroxide observed.

EXAMPLE 20

The experiment described in Example 16 was repeated with double amount of water, i.e. 2 molar equivalents (Ca 18% w/w) as opposed to 1 molar equivalent (Ca 9% w/w).

In this instance the calcium oxide was added in portions over 1 minute to the acidified glycerol-water mixture at 23.3 degrees Celsius, whilst the resulting hot suspension was agitated. The mixture thickened gradually over the next 20 minutes to form a thin paste which was poured into a container. The thin paste solidified on standing to form a white solid which could be broken into a powder (383 g).

XRD analysis of a vacuum-dried sample of the product powder showed that the solid phase consisted of mainly calcium diglyceroxide.

The results of the experiments utilising inorganic acids as additives leading to solid products which were suitable to be analysed by X-ray diffraction and described in Examples 10-20 are summarised in Table 6.

TABLE 6

| Example | Molar ratio | | | Acid | | Product composition [1] |
|---|---|---|---|---|---|---|
| | CaO | Glycerol | Water | Acid | added | |
| 10 | 2 | 2 | 1 | 1 | $H_3PO_4$ | Calcium hydrogen phosphate ($CaHPO_4$) [4] |
| | | | | | | Calcium monoglyceroxide (minor) |
| 12 | 2 [2] | 2 | 1 | 1 | $H_3PO_4$ | Mainly calcium hydrogen phosphate ($CaHPO_4$) [4] |
| | | | | | | Calcium diglyceroxide (traces) [4] |
| 13 | 2 [3] | 2 | 1 | 1 | $H_3PO_4$ | Mainly calcium hydrogen phosphate ($CaHPO_4$) [4] |
| | | | | | | Calcium monoglyceroxide and/or calcium diglyceroxide (traces) |
| 14 | 2 | 2 | 2 | 1 | $H_3PO_4$ | Calcium hydrogen phosphate ($CaHPO_4$) [4] |
| | | | | | | No detectable amount of calcium glyceroxides |
| 15 | 1 | 2 | 1 | 0.5 | $H_3PO_4$ | Calcium hydrogen phosphate ($CaHPO_4$) [4] |
| | | | | | | Calcium diglyceroxide (traces) |
| 16 | 1 | 2 | 1 | 0.5 | HCl | Mainly calcium diglyceroxide |
| | | | | | | Calcium monoglyceroxide (minor) |
| 17 | 1 | 2 | 1 | 1 | HCl | Not established |
| | | | | | | None of the known glyceroxides detected. |
| 18 | 2 | 2 | 1 | 1 | HCl | Mainly calcium hydroxide |
| | | | | | | Calcium monoglyceroxide or calcium diglyceroxide (traces) |
| 19 | 1 | 1 | 1 | 0.1 | HCl | Mainly calcium hydroxide |
| | | | | | | Calcium monoglyceroxide (minor) |
| | | | | | | Calcium diglyceroxide (minor) |
| 20 | 1 | 2 | 2 | 0.1 | HCl | Calcium diglyceroxide |

[1] Components as determined by X-ray diffraction analysis of the solid phases
[2] Blend of 0.5 molar equivalents calcium oxide and 1.5 molar equivalents calcium hydroxide
[3] Blend of 1 molar equivalent calcium oxide and 1 molar equivalent calcium hydroxide
[4] No other known calcium phosphate or calcium glycerophosphate detected in any of the samples by matching the measured patterns against the reference database The use of organic acids as additives is described in Examples 21 to 24.

EXAMPLE 21

This experiment was performed to ascertain the effect of palmitic acid addition (0.5 molar equivalents) on the composition and physical state of the product.

Experimental Procedure

A clear, colourless solution (300 g) of glycerol (273.2 g, Sigma Glycerol ReagentPlus ≥99.0% (GC)) and purified water (26.8 g, Chromasolv for HPLC, Sigma-Aldrich), i.e. with glycerol:water molar ratio of 2:1 and weight ratio of ca 91:9 and pH 7 at 20.7 degrees Celsius was charged into the stainless steel bowl of a Kenwood kMix food mixer mixing vessel equipped with blade-like agitator (without using the plastic bowl lid with port in order to avoid condensed steam water falling back into the reaction mixture) and agitated at room temperature. With the agitator running, palmitic acid flakes (205.15 g, Aldrich, 90%) was added to the wet glycerol solution over 30 seconds and the mixture agitated at room temperature for 5 minutes. A commercial grade of 94% calcium oxide (88.4 g, 1 molar equivalent) was then added to the mixture at 21.0 degrees Celsius in portions over 1 minute whilst the resulting hot suspension was agitated. The resulting white paste was agitated and changed into a hot, dough-like material after 3 minutes which started granulating after a further minute with solid material collecting on the vessel. The agitator was stopped 7 minutes after calcium oxide addition and the product left to cool to room temperature to give a white powder (557 g) with a pleasant smell.

The white powdery product was then separated by particle size into 3 fractions, i.e. Fraction 1, a free-flowing white powder (223 g) with particle size <1 mm, Fraction 2, free-flowing white granules (156 g) with particle size 1-2.36 mm and Fraction 3 with particle size >2.36 mm.

Analysis (Fraction 1)
Glycerol: 46.8% (w/w)—Method: HPLC
Calcium: 8.03% (w/w)—Method: Alkaline Metals in Foodstuffs by AAS (TM200)
Water: 7.50% (w/w)—Method: Karl Fischer (TM166)
pH (1% suspension in distilled water): 13.0—Method: TM41

X-ray diffraction analysis (XRD) of Fraction 1 powder has shown that the solid phase consisted of calcium palmitate hydrate and calcium carbonate (minor). The calcium carbonate was likely coming from the starting material calcium oxide which contained up to 4% of the carbonate as an impurity.

The experiment described in Example 21 was subsequently repeated with the additional use of 0.5 molar equivalents phosphoric acid, i.e. a molar ratio of CaO:Glycerol:Water:Palmiric acid:Phosphoric acid=1:2:1:0.5:0.5 equivalents to ascertain the effect on product compositions and physical state.

However, in this instance a pourable, cream-coloured slurry (603 g) formed which would not granulate or solidify.

EXAMPLE 22

The experiment described in Example 21 was repeated using 0.5 molar equivalents stearic acid as opposed to 0.5 molar equivalents palmitic acid.

Similar observations were made in this experiment and a white powder (576 g) with a pleasant smell was produced.

The white powdery product was separated by particle size into 3 fractions, i.e. Fraction 1, a free-flowing white powder (207 g) with particle size <1 mm, Fraction 2, free-flowing white granules (152 g) with particle size 1-2.36 mm and Fraction 3 with particle size >2.36 mm Analysis (Fraction 1)
Glycerol: 47.0% (w/w)—Method: HPLC
Calcium: 6.90% (w/w)—Method: Alkaline Metals in Foodstuffs by AAS (TM200)
Water: 7.40% (w/w)—Method: Karl Fischer (TM166)
pH (1% suspension in distilled water): 13.2—Method: TM41

X-ray diffraction analysis (XRD) of Fraction 1 powder has shown that the solid phase consisted of calcium stearate hydrate and calcium carbonate. An unidentified reflection at 10.2° in 2θ indicated there were possibly traces of calcium monoglyceroxide present. None of the other glyceroxides were detected.

EXAMPLE 23

The experiment described in Example 21 was repeated using 1 molar equivalent lactic acid as opposed to 0.5 molar equivalents palmitic acid.

In this instance the hot glycerol-water-lactic acid suspension which formed after calcium oxide addition thickened and cooled gradually over 30 minutes to form a white, cream-like paste. The material solidified on standing to give a rubbery, white solid.

X-ray diffraction analysis of a vacuum dried sample of the solid product showed that the solid phase consisted of mainly calcium lactate hydrate. No detectable amounts of the known calcium glyceroxides were observed.

EXAMPLE 24

The experiment described in Example 23 was subsequently repeated using doubling the amount of lactic acid to 2 molar equivalents.

In this instance the hot glycerol-water-lactic acid suspension which formed after calcium oxide addition also thickened and cooled gradually over 30 minutes to form a white, cream-like paste which changed into a rubbery, granular substance on standing.

Analysis
Glycerol: 44.9% (w/w)—Method: HPLC
Calcium: 5.80% (w/w)—Method: Alkaline Metals in Foodstuffs by AAS (TM200)
Water: 9.30% (w/w)—Method: Karl Fischer (TM166)
pH (1% suspension in distilled water): 12.2—Method: TM41

X-ray diffraction analysis of a vacuum-dried sample (white powder) of the solid product showed that the solid phase consisted of mainly calcium lactate hydrate. No detectable amounts of the known calcium glyceroxides were observed.

It was possible to transform the rubbery granules into non-sticky and uniform, free-flowing powders solid by mixing it in suitable ratios with other free-flowing powders produced in previous experiments. Examples of (non-optimised) uniform, free-flowing powders mixtures that could be produced in this way with an indication of calculated glycerol, calcium, and water contents and composition in the solid forms are depicted in Table 7.

TABLE 7

| Mixing agent (Example No) | Mixing agent % w/w | Glycerol % w/w | Calcium % w/w | Water % w/w | Ingredients (solid phase) |
| --- | --- | --- | --- | --- | --- |
| 24 | 100 (reference) | 44.9 | 5.8 | 9.3 | Calcium lactate hydrate |
| 3 | 70 | 67.49 | 15.11 | 7.03 | Calcium lactate hydrate Calcium diglyceroxide |
| 3 | 100 (reference) | 77.2 | 19.1 | 6.05 | Calcium diglyceroxide |
| 14 | 60 | 47.60 | 16.54 | 7.28 | Calcium lactate hydrate Calcium hydrogen phosphate $(CaHPO_4)$ [4)] |
| 14 | 100 (reference) | 49.4 | 23.7 | 5.93 | Calcium hydrogen phosphate $(CaHPO_4)$ [4)] |
| 21 | 70 | 46.23 | 7.34 | 8.04 | Calcium lactate hydrate Calcium palmitate hydrate |
| 21 | 100 (reference) | 46.8 | 8.0 | 7.5 | Calcium palmitate hydrate |

TABLE 7-continued

| Mixing agent (Example No) | Mixing agent % w/w | Glycerol % w/w | Calcium % w/w | Water % w/w | Ingredients (solid phase) |
|---|---|---|---|---|---|
| 22 | 70 | 46.37 | 6.57 | 7.97 | Calcium lactate hydrate Calcium stearate hydrate |
| 22 | 100 (reference) | 47.0 | 6.9 | 7.4 | Calcium stearate hydrate |

The results of the experiments utilising organic acids as additives leading to solid products which were suitable to be analysed by X-ray diffraction and described in Examples 21-24 are summarised in Table 8.

TABLE 8

| | Molar ratio | | | Acid | | |
|---|---|---|---|---|---|---|
| Example | CaO | Glycerol | Water | Acid | added | Product composition[1] |
| 21 | 1 | 2 | 1 | 0.5 | Palmitic | Mainly calcium palmitate hydrate Calcium carbonate (minor). |
| 22 | 1 | 2 | 1 | 0.5 | Stearic | Calcium stearate hydrate Calcium carbonate Possibly traces of calcium monoglyceroxide None of the other glyceroxides detected |
| 23 | 1 | 2 | 1 | 1 | Lactic | Mainly calcium lactate hydrate None of the known calcium glyceroxides detected |
| 24 | 2 | 2 | 1 | 2 | Lactic | Mainly calcium lactate hydrate None of the known calcium glyceroxides detected |

[1]Components as determined by X-ray diffraction analysis of the solid phases

It is an advantage of the invention illustrated that wet glycerol, which is produced in the production of bio-diesel and which is regarded as a waste product, can be used to produce, in an energy efficient and environmentally friendly manner, commercially useful particulate materials which are easier to handle and less costly to transport than wet glycerol and which in turn can be used as intermediates for further processing.

The invention claimed is:

1. A method of producing a solid glycerol derived material, the method comprising the step of adding wet glycerol produced as a by-product of the production of biodiesel or from a source of wet glycerol and a metal oxide into a reaction vessel for combining therein, the metal oxide optionally containing a metal hydroxide, the glycerol having a water content of between about 5 and 50%, and the molar ratio rate of the metal oxide to the water being between 0.1 and 10 so that an exothermic reaction is produced in which at least part of the water present in the glycerol reacts with the metal oxide in the exothermic reaction and at least part is driven off by heat produced in the exothermic reaction to produce the solid glycerol derived material, wherein the content of glycerol in said solid glycerol derived material is at least 44.9% (w/w).

2. A method as claimed in claim 1, in which the glycerol having a water content of between 5% and 50% is produced as a by-product of the production of bio-diesel.

3. A method as claimed in claim 1, in which the glycerol has a water content of between 9% and 18%.

4. A method as claimed in claim 1, in which the metal oxide is selected from Group 1A metal oxides, Group 2A metal oxides, transition metal oxides and combinations thereof.

5. A method as claimed in claim 4, in which the metal oxide is calcium oxide.

6. A method as claimed in claim 5, in which the calcium oxide has a purity of at least 75%.

7. A method as claimed in claim 1, in which the solid product is a particulate material.

8. A method as claimed in claim 1, further comprising combining the glycerol and the metal oxide with at least one additional component, the or each additional component being selected from inorganic acids, organic acids and mixtures thereof.

9. A method as claimed in claim 8, in which the inorganic acids are selected from phosphoric acid, sulphuric acid and hydrochloric acid.

10. A method as claimed in claim 9, in which the organic acids are selected from alkyl carboxylic acids, hydroxyalkyl carboxylic acids and amino acids.

11. A method as claimed in claim 10, in which the organic acids are selected from propionic acid, lactic acid, palmitic acid and stearic acid.

12. A method as claimed in claim 8, in which the glycerol and the metal oxide and, optionally, the or each additional component are rapidly combined over a period of between 1 second and 6 minutes to produce a reaction mixture, the reaction mixture is rapidly agitated for a period of between 1 second and 10 minutes and the reaction mixture is then rapidly discharged over a period of between 1 and 60 seconds.

13. A method as claimed in claim 8, in which a pre-determined quantity of glycerol and, optionally, the or each additional component are added to a reaction vessel and the metal oxide is added over a period of between 1 and 60 minutes to produce a reaction mixture.

14. A method as claimed in claim 8, in which the glycerol and, optionally, the or each additional component and the metal oxide are added to a reaction vessel in separate streams to produce a reaction mixture, and the mixture is periodically removed from the reaction vessel at intervals of between 1 and 60 minutes so that an approximately constant level of product is maintained in the reaction vessel.

15. A method as claimed in claim 8, in which the glycerol and the metal oxide and, optionally, the or each additional component are rapidly pre-mixed and added to a reaction vessel to produce a reaction mixture, and the mixture is periodically removed from the reaction vessel at intervals of between 1 and 60 minutes so that an approximately constant level of product is maintained in the reaction vessel.

16. A method as claimed in claim 10, in which a portion of the product produced is recycled back into the reaction vessel on a continuous basis.

17. A method as claimed in claim 8, in which the molar ratio between the additional component or combination of additional components per 1 molar equivalent of metal oxide or metal oxide-metal hydroxide mixture is between 0.001 and 2 molar equivalents.

18. A method as claimed in claim 17, in which the molar ratio is between 0.1 and 1 molar equivalent.

19. A method as claimed in claim 1, in which the solid glycerol derived material is selected from either calcium monoglyceroxide, calcium diglyceroxide, tricalcium octaglyceroxide and mixtures thereof or salts of the inorganic acids, organic acids and mixtures thereof combined with glycerol, or mixtures thereof.

* * * * *